US011699516B2

(12) United States Patent
Kado

(10) Patent No.: US 11,699,516 B2
(45) Date of Patent: *Jul. 11, 2023

(54) MEDICAL IMAGE PROCESSING APPARATUS, MEDICAL OBSERVATION APPARATUS, AND IMAGE PROCESSING METHOD

(71) Applicant: Sony Olympus Medical Solutions Inc., Tokyo (JP)

(72) Inventor: Masataka Kado, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 77 days.

This patent is subject to a terminal disclaimer.

(21) Appl. No.: 17/376,183

(22) Filed: Jul. 15, 2021

(65) Prior Publication Data
US 2021/0343399 A1 Nov. 4, 2021

Related U.S. Application Data

(63) Continuation of application No. 16/259,023, filed on Jan. 28, 2019, now Pat. No. 11,328,811.

(30) Foreign Application Priority Data

Mar. 12, 2018 (JP) .................. 2018-044716

(51) Int. Cl.
*G16H 30/40* (2018.01)
*G06T 7/00* (2017.01)
(Continued)

(52) U.S. Cl.
CPC ............... *G16H 30/40* (2018.01); *A61B 3/10* (2013.01); *G06T 7/0012* (2013.01); *A61B 3/0008* (2013.01); *A61B 3/18* (2013.01)

(58) Field of Classification Search
CPC .......... G16H 30/40; G16H 20/40; A61B 3/10; A61B 3/13; A61B 3/0008; A61B 3/18;
(Continued)

(56) References Cited

U.S. PATENT DOCUMENTS 5,163,076 A * 11/1992 Koyama .................. H05G 1/60
378/98.12
6,243,207 B1 * 6/2001 Kawamura ........ G02B 27/0149
348/E13.058
(Continued)

FOREIGN PATENT DOCUMENTS

JP 2005-049646 A 2/2005
JP 2014022806 A 2/2014
(Continued)

*Primary Examiner* — Congvan Tran
(74) *Attorney, Agent, or Firm* — Xsensus LLP

(57) ABSTRACT

There is provided a medical image processing apparatus including: an association processing section configured to associate multiple medical captured images in which an observation target is imaged by each of multiple imaging devices including imaging devices in which one or both of an in-focus position and an in-focus range are different; and a compositing processing section configured to depth-composite each of a medical captured image for a right eye and a medical captured image for a left eye among the multiple medical captured images by using an associated other medical captured image.

22 Claims, 10 Drawing Sheets

(51) Int. Cl.
*A61B 3/10* (2006.01)
*A61B 3/00* (2006.01)
*A61B 3/18* (2006.01)

(58) Field of Classification Search
CPC ......... G06T 7/0012; G06T 5/50; G06T 5/003; G06T 2207/10012; G06T 2207/30096; G06T 2207/10068
See application file for complete search history.

(56) References Cited

U.S. PATENT DOCUMENTS

| | | | |
|---|---|---|---|
| 7,768,702 B2 | 8/2010 | Hirose et al. | |
| 10,073,515 B2 | 9/2018 | Awdeh | |
| 10,631,725 B2 | 4/2020 | Walsh et al. | |
| 2002/0047835 A1* | 4/2002 | Kawai | H04N 13/279 |
| | | | 345/204 |
| 2007/0058249 A1 | 3/2007 | Hirose et al. | |
| 2009/0259102 A1 | 10/2009 | Koninckx | |
| 2012/0069004 A1* | 3/2012 | Takama | H04N 13/128 |
| | | | 345/419 |
| 2012/0249534 A1* | 10/2012 | Kanagawa | H04N 13/398 |
| | | | 345/419 |
| 2013/0010059 A1* | 1/2013 | Kobayashi | G06T 19/20 |
| | | | 348/E13.064 |
| 2013/0250067 A1 | 9/2013 | Laxhuber et al. | |
| 2014/0128731 A1 | 5/2014 | Gonzalez et al. | |
| 2014/0211158 A1 | 7/2014 | Oyaizu et al. | |
| 2016/0058397 A1 | 3/2016 | Kim | |
| 2016/0220324 A1 | 8/2016 | Tesar | |
| 2017/0020627 A1 | 1/2017 | Tesar | |
| 2017/0065352 A1 | 3/2017 | Razzaque et al. | |
| 2017/0143442 A1 | 5/2017 | Tesar | |
| 2018/0146183 A1 | 5/2018 | Zhou | |
| 2018/0256145 A1 | 9/2018 | Tesar et al. | |
| 2019/0246093 A1 | 8/2019 | Shiraki et al. | |
| 2019/0328208 A1 | 10/2019 | Kashima et al. | |
| 2020/0015655 A1 | 1/2020 | Taguchi | |
| 2020/0093545 A1 | 3/2020 | Sakaguchi et al. | |
| 2020/0326540 A1* | 10/2020 | Sumigama | G02B 27/017 |

FOREIGN PATENT DOCUMENTS

| | | |
|---|---|---|
| JP | 2015521913 A | 8/2015 |
| WO | WO2017145531 A1 | 8/2017 |
| WO | WO2017217115 A1 | 12/2017 |

* cited by examiner

MEDICAL IMAGE PROCESSING APPARATUS, MEDICAL OBSERVATION APPARATUS, AND IMAGE PROCESSING METHOD

This application is a continuation of U.S. application Ser. No. 16/259,023, filed Jan. 28, 2019, now U.S. Pat. No. 11,328,811, issued on May 10, 2022, which claims the benefit of Japanese Priority Patent Application JP 2018-044716 filed Mar. 12, 2018, the entire contents of each are incorporated herein by reference.

BACKGROUND

The present disclosure relates to a medical image processing apparatus, a medical observation apparatus, and an image processing method.

Recently, in the medical field, to support microsurgery such as neurosurgical procedures, or to perform an endoscopic surgery, for example, medical observation apparatus capable of enlarged observation of an observation target such as an affected area are used in some cases. Examples of medical observation apparatus include a medical observation apparatus provided with an optical microscope, and a medical observation apparatus provided with an imaging device that functions as an electronic imaging microscope. In the following, the above medical observation apparatus provided with an optical microscope will be designated an "optical medical observation apparatus". Also, in the following, the above medical observation apparatus provided with an imaging device will be designated an "electronic imaging medical observation apparatus" or simply a "medical observation apparatus" in some cases. Also, in the following, a captured image (a moving image or a still image; the same applies hereinafter) in which an observation target is captured by an imaging device provided in a medical observation apparatus is denoted a "medical captured image".

With an electronic imaging medical observation apparatus, along with the increased image quality of imaging devices, the increased image quality of display apparatus on which captured images are displayed, and the like, the same or higher image quality than an optical medical observation apparatus has come to be obtained. Also, because a user who uses an electronic imaging medical observation apparatus (for example, medical personnel such as a surgeon or a surgeon's assistant) is not required to peer into an eyepiece lens included in an optical microscope like in the case of using an optical medical observation apparatus, it is possible to move the position of the imaging device more freely. For this reason, using an electronic imaging medical observation apparatus has an advantage of enabling more flexible support of microsurgery, and in the medical field, utilization of electronic imaging medical observation apparatus is progressing.

Among these, there is being developed technology related to an observation apparatus that obtains a stereoscopic image with which an observer is able to focus on an observation image over a wide range with little strain. Examples of the above technologies include the technology described in JP 2005-49646A.

SUMMARY

In imaging devices provided in medical observation apparatus, as higher pixel counts and higher pixel densities are achieved to improve image quality, the resolution increases, but there is a tendency for the depth of field to become shallower. At this point, by reducing the aperture (increasing the f-number), it is possible to deepen the depth of field. However, if the depth of field is deepened as above, the medical captured image becomes dark, and in addition, the resolution is lowered due to the influence of diffraction.

As a first method of potentially achieving both a deeper depth of field and a higher resolution, a "method of imaging a deep depth and a shallow depth at the same time by optical path separation and compositing the obtained captured images" is conceivable, for example. However, the above method leads to bulkier equipment. Also, as another method of potentially achieving both a deeper depth of field and a higher resolution, a "method of varying the aperture size in two imaging devices, and causing the observer looking at the captured images to recognize a captured image of shallow depth with the right eye and a captured image of deep depth with the left eye, such that the captured images are composited in the mind" is conceivable, for example. However, with the other method above, there is a possibility that the observer will experience strain, and in addition, since the other method above is not a method of processing the captured images, the method is not desirable from the perspective of saving and utilizing the captured images.

The present disclosure proposes a novel and improved medical image processing apparatus, medical observation apparatus, and image processing method capable of potentially achieving both a deeper depth of field and a higher resolution in each of a medical captured image for the right eye and a medical captured image for the left eye.

According to an embodiment of the present disclosure, there is provided a medical image processing apparatus including: an association processing section configured to associate multiple medical captured images in which an observation target is imaged by each of multiple imaging devices including imaging devices in which one or both of an in-focus position and an in-focus range are different; and a compositing processing section configured to depth-composite each of a medical captured image for a right eye and a medical captured image for a left eye among the multiple medical captured images by using an associated other medical captured image.

In addition, according to an embodiment of the present disclosure, there is provided a medical observation apparatus including: multiple imaging devices, each configured to image an observation target, including imaging devices in which one or both of an in-focus position and an in-focus range are different; an association processing section configured to associate multiple medical captured images captured by each of the multiple imaging devices; and a compositing processing section configured to depth-composite each of a medical captured image for a right eye and a medical captured image for a left eye among the multiple medical captured images by using an associated other medical captured image.

In addition, according to an embodiment of the present disclosure, there is provided an image processing method, executed by a medical image processing apparatus, including: associating multiple medical captured images in which an observation target is imaged by each of multiple imaging devices including imaging devices in which one or both of an in-focus position and an in-focus range are different; and depth-compositing each of a medical captured image for a right eye and a medical captured image for a left eye among the multiple medical captured images by using an associated other medical captured image.

According to an embodiment of the present disclosure, both a deeper depth of field and a higher resolution in each of a medical captured image for the right eye and a medical captured image for the left eye can be potentially achieved.

Note that the effects described above are not necessarily limitative. With or in the place of the above effects, there may be achieved any one of the effects described in this specification or other effects that may be grasped from this specification.

DETAILED DESCRIPTION OF THE EMBODIMENT(S)

Figure 1:
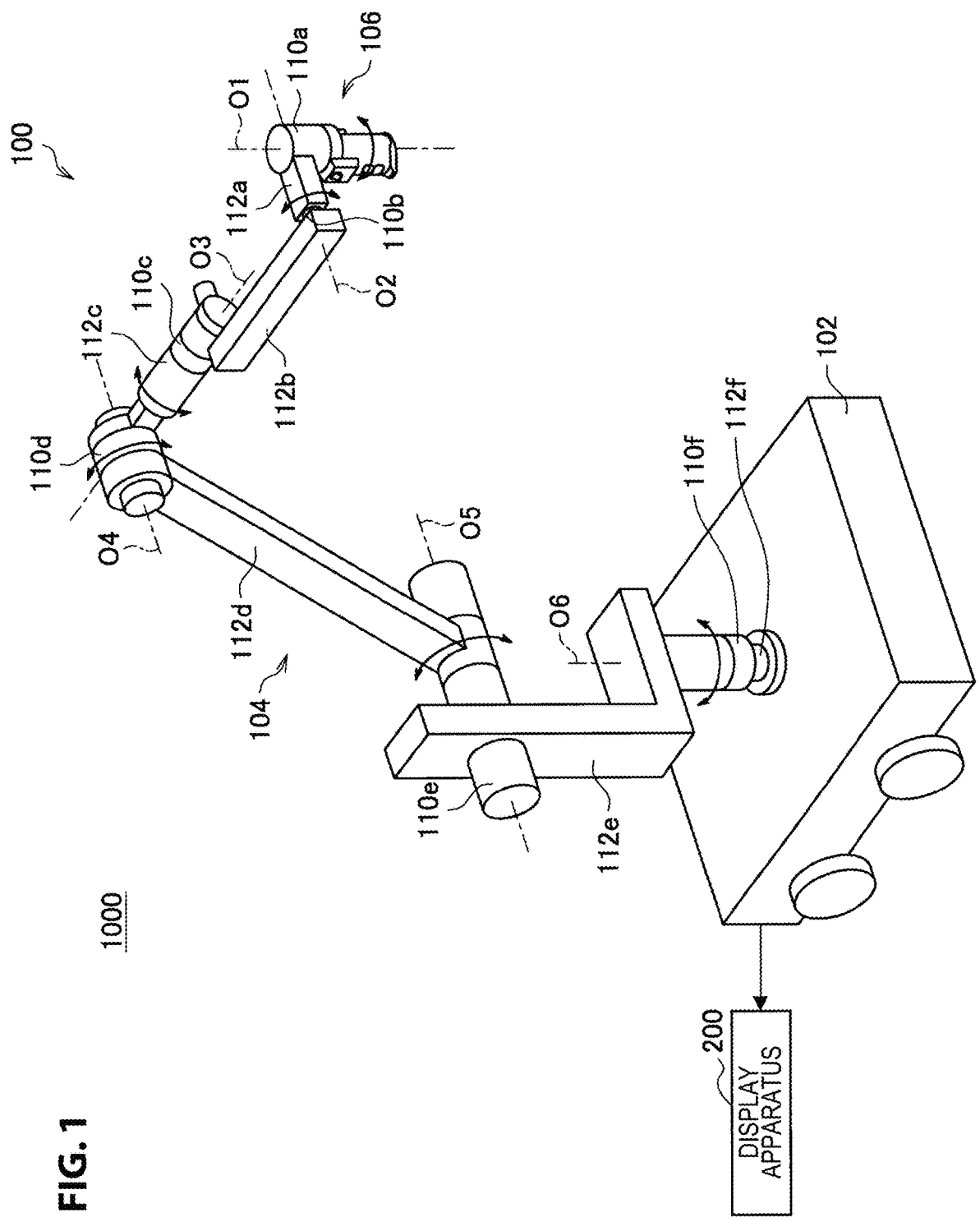
FIG. 1 is an explanatory diagram illustrating a first example of a configuration of a medical observation system according to the present embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description hereinafter will proceed in the following order.

1. Medical observation system according to present embodiment and image processing method according to present embodiment
   [1] Configuration of medical observation system
      [1-1] Medical observation system according to first example
      [1-2] Medical observation system according to second example
      [1-3] Medical observation system according to other example
      [1-4] Functional configuration of medical observation apparatus
   [2] Image processing method according to present embodiment
      [2-1] Processes related to image processing method according to present embodiment
      [2-2] Example of processes related to image processing method according to present embodiment
   [3] Example of advantageous effects exhibited by use of image processing method according to present embodiment
2. Program according to present embodiment (Medical Observation System According to Present Embodiment and Image Processing Method According to Present Embodiment)

Hereinafter, an example of a medical observation system according to the present embodiment will be described, while an image processing method according to the present embodiment will also be described.

Hereinafter, the case in which the medical observation apparatus according to the present embodiment executes processes related to the image processing method according to the present embodiment, that is, the case in which the medical observation apparatus according to the present embodiment functions as a medical image processing apparatus will be described primarily. Note that in the medical observation system according to the present embodiment, the apparatus that functions as the medical image processing apparatus is not limited to the medical observation apparatus according to the present embodiment. For example, in the medical observation system according to the present embodiment, the display apparatus described later may also function as the medical image processing apparatus that executes the processes related to the image processing method according to the present embodiment. For example, in the medical observation system according to the present embodiment, any apparatus capable of executing the processes related to the image processing method according to the present embodiment, such as a medical controller, may function as the medical image processing apparatus.

[1] Configuration of Medical Observation System

[1-1] Medical Observation System According to First Example

FIG. 1 is an explanatory diagram illustrating a first example of the configuration of a medical observation system 1000 according to the present embodiment. The medical observation system 1000 illustrated in FIG. 1 includes a medical observation apparatus 100 and a display apparatus 200, for example.

Note that the medical observation system according to the first example is not limited to the example illustrated in FIG. 1.

For example, the medical observation system according to the first example additionally may include a medical control apparatus (not illustrated) that controls various operations in the medical observation apparatus 100. In the medical observation system 1000 illustrated in FIG. 1, as described later, an example is illustrated in which, by providing the medical observation apparatus 100 with a control section (described later), the medical observation apparatus 100 includes the functions of the medical control apparatus (not illustrated).

Examples of the medical control apparatus (not illustrated) include, a "medical controller", a "computer such as a server", and the like. Also, the medical control apparatus (not illustrated) may be, for example, an integrated circuit (IC) that can be embedded in equipment like the above.

Additionally, the medical observation system according to the first example may also be a configuration that includes one or both of the medical observation apparatus 100 and the display apparatus 200. In the case of including multiple medical observation apparatuses 100, in each medical observation apparatus 100, processes according to the image processing method described later are performed. Also, in the case in which the medical observation system according to the first example is a configuration that includes multiple medical observation apparatuses 100 and display apparatuses 200, the medical observation apparatus 100 and the display apparatus 200 may be associated in a 1-to-1 manner, or multiple medical observation apparatuses 100 may be associated with a single display apparatus 200. In the case in which multiple medical observation apparatuses 100 are associated with a single display apparatus 200, which medical observation apparatus 100 provides a medical captured image to be displayed on a display screen is switched by performing a switching operation or the like in the display apparatus 200, for example.

Hereinafter, each apparatus included in the medical observation system 1000 according to the first example illustrated in FIG. 1 will be described.

[1-1-1] Display Apparatus 200

The display apparatus 200 is a display device in the medical observation system 1000 according to the first example, and corresponds to an external display device from the perspective of the medical observation apparatus 100. The display apparatus 200 displays various images on a display screen, such as a medical captured image taken in the medical observation apparatus 100, or an image related to a user interface (UI), for example. Also, the display apparatus 200 may include a configuration capable of 3D display according to any method. The display on the display apparatus 200 is controlled by, for example, the medical observation apparatus 100 or the medical control apparatus (not illustrated).

In the medical observation system 1000, the display apparatus 200 is installed in an arbitrary location visible to a person involved in a surgery inside an operating room, such as on a wall, the ceiling, or the floor of the operating room.

Examples of the display apparatus 200 include a liquid crystal display, an organic electro-luminescence (EL) display, a cathode ray tube (CRT) display, and the like.

Note that the display apparatus 200 is not limited to the example illustrated above. For example, the display apparatus 200 may also be an arbitrary wearable apparatus that is used by being worn on the body of the surgeon or the like, such as a head-mounted display, an eyewear-type apparatus, or the like.

The display apparatus 200 runs on electric power supplied from an internal power source such as a battery provided in the display apparatus 200, on electric power supplied from a connected external power source, or the like, for example.

[1-1-2] Medical Observation Apparatus 100

The medical observation apparatus 100 illustrated in FIG. 1 is an electronic imaging medical observation apparatus. For example, in the case in which the medical observation apparatus 100 illustrated in FIG. 1 is used during surgery, the surgeon (one example of the user of the medical observation apparatus 100) observes an operating site (an affected area) while referring to a medical captured image which has been taken by the medical observation apparatus 100 and displayed on the display screen of the display apparatus 200, and performs various treatments, such as techniques depending on the surgical procedure, on the operating site.

As illustrated in FIG. 1, the medical observation apparatus 100 is provided with a base 102, an arm 104, and an imaging device 106, for example.

Additionally, although not illustrated in FIG. 1, the medical observation apparatus 100 may also be provided with, for example, one or multiple processors (not illustrated) including a computational circuit such as a microprocessing unit (MPU), read-only memory (ROM; not illustrated), random access memory (RAM; not illustrated), a recording medium (not illustrated), and a communication device (not illustrated). The medical observation apparatus 100 runs on electric power supplied from an internal power source such as a battery provided in the medical observation apparatus 100, on electric power supplied from a connected external power source, or the like, for example.

The one or multiple processors (not illustrated) function as the control section in the medical observation apparatus 100 (described later). The ROM (not illustrated) stores programs and control data such as computational parameters used by the one or multiple processors (not illustrated). The RAM (not illustrated) temporarily stores programs executed by the one or multiple processors (not illustrated), or the like.

The recording medium (not illustrated) functions as a storage section (not illustrated) in the medical observation apparatus 100. A variety of data is stored on the recording medium (not illustrated), including data related to the image processing method according to the present embodiment, and various applications, for example. Herein, examples of the recording medium (not illustrated) include a magnetic recording medium such as a hard disk, non-volatile memory such as flash memory, and the like. Additionally, the recording medium (not illustrated) may also be removable from the medical observation apparatus 100.

The communication device (not illustrated) is a communication device provided in the medical observation apparatus 100, and fulfills a role of communicating in a wireless or wired manner with an external apparatus such as the display apparatus 200. Herein, examples of the communication device (not illustrated) include an IEEE 802.15.1 port and transmitting-receiving circuit (wireless communication), an IEEE 802.11 port and transmitting-receiving circuit (wireless communication), a communication antenna and a RF circuit (wireless communication), a LAN terminal and a transmitting-receiving circuit (wired communication), and the like.

[1-1-2-1] Base 102

The base 102 is the base of the medical observation apparatus 100. One end of the arm 104 is connected to the base 102, and the base 102 supports the arm 104 and the imaging device 106.

Also, casters are provided on the base 102, for example, and the medical observation apparatus 100 contacts the floor through the casters. By providing the casters, the medical observation apparatus 100 is able to move easily over the floor by the casters.

[1-1-2-2] Arm 104

The arm 104 includes multiple links joined to each other by joint sections.

In addition, the arm 104 supports the imaging device 106. The imaging device 106 supported by the arm 104 is movable three-dimensionally, and after moving, the position and the attitude of the imaging device 106 are maintained by the arm 104.

More specifically, the arm 104 includes, for example, multiple joint sections 110*a*, 110*b*, 110*c*, 110*d*, 110*e*, and 110*f*, and multiple links 112*a*, 112*b*, 112*c*, 112*e*, and 112*f* rotatably joined to each other by the joint sections 110*a*, 110*b*, 110*c*, 110*d*, 110*e*, and 110*f*. The rotatable range of each of the joint sections 110*a*, 110*b*, 110*c*, 110*d*, 110*e*, and 110*f* is set arbitrarily during the design stage, the manufacturing stage, or the like so that the desired motion of the arm 104 is realized.

In other words, in the medical observation apparatus 100 illustrated in FIG. 1, six degrees of freedom are realized in relation to the movement of the imaging device 106 by six rotation axes (first axis O1, second axis O2, third axis O3, fourth axis O4, fifth axis O5, and sixth axis O6) corresponding to the six joint sections 110*a*, 110*b*, 110*c*, 110*d*, 110*e*, and 110*f* included in the arm 104. More specifically, in the medical observation apparatus 100 illustrated in FIG. 1, motion with six degrees of freedom, including three degrees of translational freedom and three degrees of rotational freedom, is realized.

Actuators (not illustrated) are provided in each of the joint sections 110*a*, 110*b*, 110*c*, 110*d*, 110*e*, and 110*f*. Each of the joint sections 110*a*, 110*b*, 110*c*, 110*d*, 110*e*, and 110*f* rotates about the corresponding rotation axis by the driving of the actuators (not illustrated). The driving of the actuators (not illustrated) is controlled by, for example, a processor that functions as the control section described later, or an external medical control apparatus (not illustrated).

Each of the joint sections 110*a*, 110*b*, 110*c*, 110*d*, 110*e*, and 110*f* may be provided with angle sensors (not illustrated) capable of detecting a rotational angle for each of six rotation axes. The angle sensors may be, for example, rotary encoders, or any sensors capable of obtaining a rotational angle for each of six rotation axes, such as angular velocity sensors.

By having each of the joint sections 110*a*, 110*b*, 110*c*, 110*d*, 110*e*, 110*f* rotate about the corresponding rotation axis by the driving of the actuators (not illustrated), various operations of the arm 104, such as extending and contracting (folding up) the arm 104, for example, are realized.

The joint section 110*a* has an approximately cylindrical shape, and supports the imaging device 106 (the top end of the imaging device 106 in FIG. 1) on the front end portion of the joint section 110*a* (the bottom end portion in FIG. 1), so as to allow revolution about a rotation axis (first axis O1) parallel to the central axis of the imaging device 106. Herein, the medical observation apparatus 100 is configured so that the first axis O1 is aligned with the optical axis in the imaging device 106. In other words, by causing the imaging device 106 to revolve about the first axis O1 illustrated in FIG. 1, the medical captured image captured by the imaging device 106 becomes an image which has changed so that the field of view rotates.

The link 112*a* is an approximately rod-shaped member, and securely supports the joint section 110*a*. The link 112*a* extends in a direction orthogonal to the first axis O1, for example, and is connected to the joint section 110*b*.

The joint section 110*b* has an approximately cylindrical shape, and supports the link 112*a* so as to allow revolution about a rotation axis (second axis O2) orthogonal to the first axis O1. Also, the link 112*b* is securely connected to the joint section 110*b*.

The link 112*b* is an approximately rod-shaped member, and extends in a direction orthogonal to the second axis O2. Also, each of the joint section 110*b* and the joint section 110*c* is connected to the link 112*b*.

The joint section 110*c* has an approximately cylindrical shape, and supports the link 112*b* so as to allow revolution about a rotation axis (third axis O3) mutually orthogonal to each of the first axis O1 and the second axis O2. Also, one end of the link 112*c* is securely connected to the joint section 110*c*.

Herein, by having the front end side (the side on which the imaging device 106 is provided) of the arm 104 revolve about the second axis O2 and the third axis O3, the imaging device 106 can be made to move so that the position of the imaging device 106 in the horizontal plane is changed. In other words, in the medical observation apparatus 100, controlling the rotation about the second axis O2 and the third axis O3 makes it possible to move the field of view of the medical captured image in a flat plane.

The link 112*c* is a member in which one end has an approximately cylindrical shape, and the other end has an approximately rod-like shape. On the side of the one end of the link 112*c*, the joint section 110*c* is securely connected so that the central axis of the joint section 110*c* and the central axis of the approximately cylindrical shape are the same. Also, on the side of the other end of the link 112*c*, the joint section 110*d* is connected.

The joint section 110*d* has an approximately cylindrical shape, and supports the link 112*c* so as to allow revolution about a rotation axis (fourth axis O4) orthogonal to the third axis O3. The link 112*d* is securely connected to the joint section 110*d*.

The link 112*d* is an approximately rod-shaped member, and extends orthogonally to the fourth axis O4. One end of the link 112*d* is securely connected to the joint section 110*d* so as to abut the approximately cylindrical side face of the joint section 110*d*. Also, the joint section 110*e* is connected to the other end of the link 112*d* (the end on the opposite side of the side where the joint section 110*d* is connected).

The joint section 110*e* has an approximately cylindrical shape, and supports one end of the link 112*d* so as to allow revolution about a rotation axis (fifth axis O5) parallel to the fourth axis O4. Also, one end of the link 112*e* is securely connected to the joint section 110*e*.

Herein, the fourth axis O4 and the fifth axis O5 are rotation axis about which the imaging device 106 may be moved in the vertical direction. By having the front end side (the side on which the imaging device 106 is provided) of the arm 104 revolve about the fourth axis O4 and the fifth axis O5, the position of the imaging device 106 in the vertical direction changes. Thus, by having the front end side (the side on which the imaging device 106 is provided) of the arm 104 revolve about the fourth axis O4 and the fifth axis O5, changing the distance between the imaging device 106 and an observation target, such as an operating site of a patient, becomes possible.

The link 112*e* is a member that includes a combination of a first member having an approximate L-shape with one edge extending in the vertical direction while the other edge extends in the horizontal direction, and a rod-like second member that extends vertically downward from the part of the first member that extends in the horizontal direction. The joint section 110*e* is securely connected to the part of the first member of the link 112*e* that extends in the vertical direction. Also, the joint section 110*f* is connected to the second member of the link 112*e*.

The joint section 110*f* has an approximately cylindrical shape, and supports the link 112*e* so as to allow revolution about a rotation axis (sixth axis O6) parallel to the vertical direction. Also, the link 112*f* is securely connected to the joint section 110*f*.

The link 112*f* is an approximately rod-shaped member, and extends in the vertical direction. The joint section 110*f* is connected to one end of the link 112*f*. Also, the other end of the link 112*f* (the end on the opposite side of the side where the joint section 110*f* is connected) is securely connected to the base 102.

By having the arm 104 include the configuration indicated above, in the medical observation apparatus 100, six degrees of freedom are realized with respect to the movement of the imaging device 106.

Note that the configuration of the arm 104 is not limited to the example indicated above.

For example, each of the joint sections 110a, 110b, 110c, 110d, 110e, and 110f of the arm 104 may be provided with a brake that restrains rotation in each of the joint sections 110a, 110b, 110c, 110d, 110e, and 110f. The brake according to the present embodiment may be a brake of an arbitrary method, such as a mechanically driven brake or an electrically driven electromagnetic brake, for example.

The driving of the above brakes is controlled by, for example, a processor that functions as the control section described later, or an external medical control apparatus (not illustrated). By controlling the driving of the above brakes, in the medical observation apparatus 100, the operating mode of the arm 104 is set. Examples of operating modes of the arm 104 include a locked mode and a free mode.

Herein, the locked mode according to the present embodiment is, for example, an operating mode in which the position and the attitude of the imaging device 106 are locked by using brakes to restrain rotation about each rotation axis provided in the arm 104. By having the arm 104 enter the locked mode, the operating state of the medical observation apparatus 100 becomes a locked state in which the position and the attitude of the imaging device 106 are locked.

Also, the free mode according to the present embodiment is an operating mode in which the above brakes are released, thereby allowing each rotation axis provided in the arm 104 to rotate freely. For example, in the free mode, the position and the attitude of the imaging device 106 are adjustable by direct operations performed by the surgeon. Herein, a direct operation according to the present embodiment means, for example, an operation in which the surgeon grips the imaging device 106 with his or her hand, and directly moves the imaging device 106.

[1-1-2-3] Imaging Device 106

The imaging device 106 is supported by the arm 104, and images an observation target such as an operating site of a patient, for example. Imaging in the imaging device 106 is controlled by, for example, a processor that functions as the control section described later, or an external medical control apparatus (not illustrated).

The imaging device 106 has a configuration corresponding to an electronic imaging microscope, for example.

Figure 2:
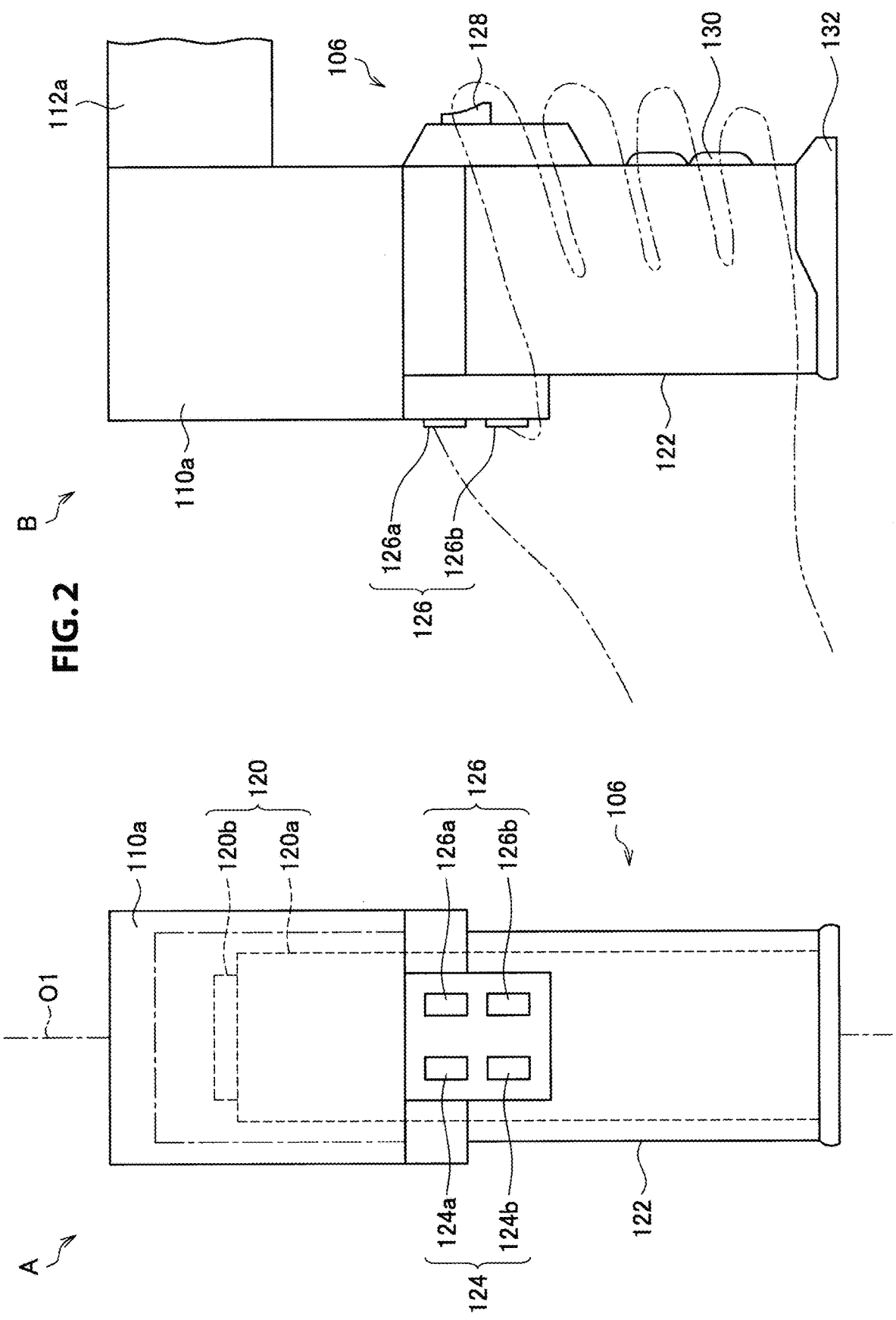
FIG. 2 is an explanatory diagram for explaining an example of the configuration of an imaging device provided in a medical observation apparatus according to the present embodiment.
Figure 3:
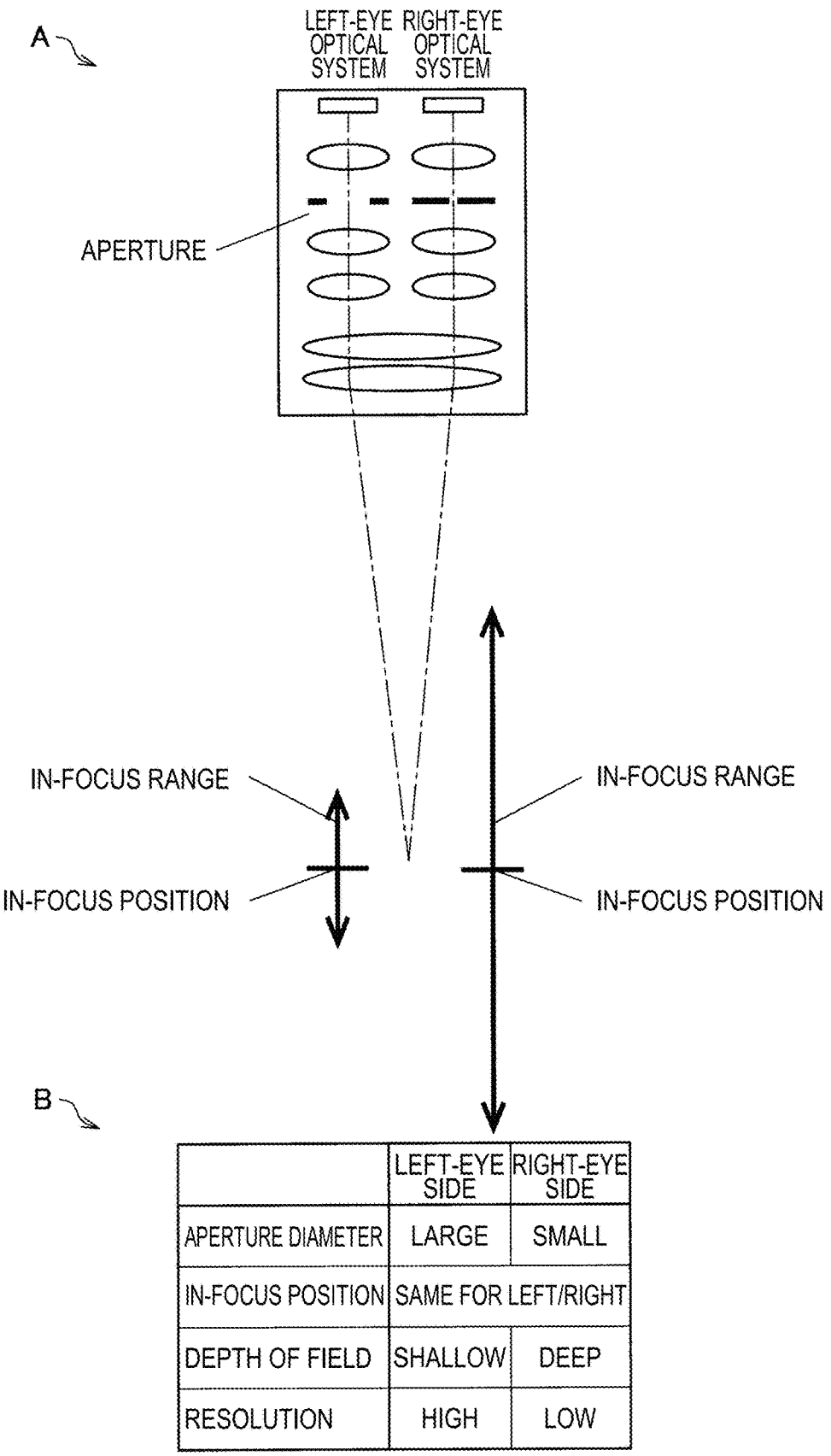
FIG. 3 is an explanatory diagram illustrating one example of an imaging device that functions as a stereo camera.
Figure 4:
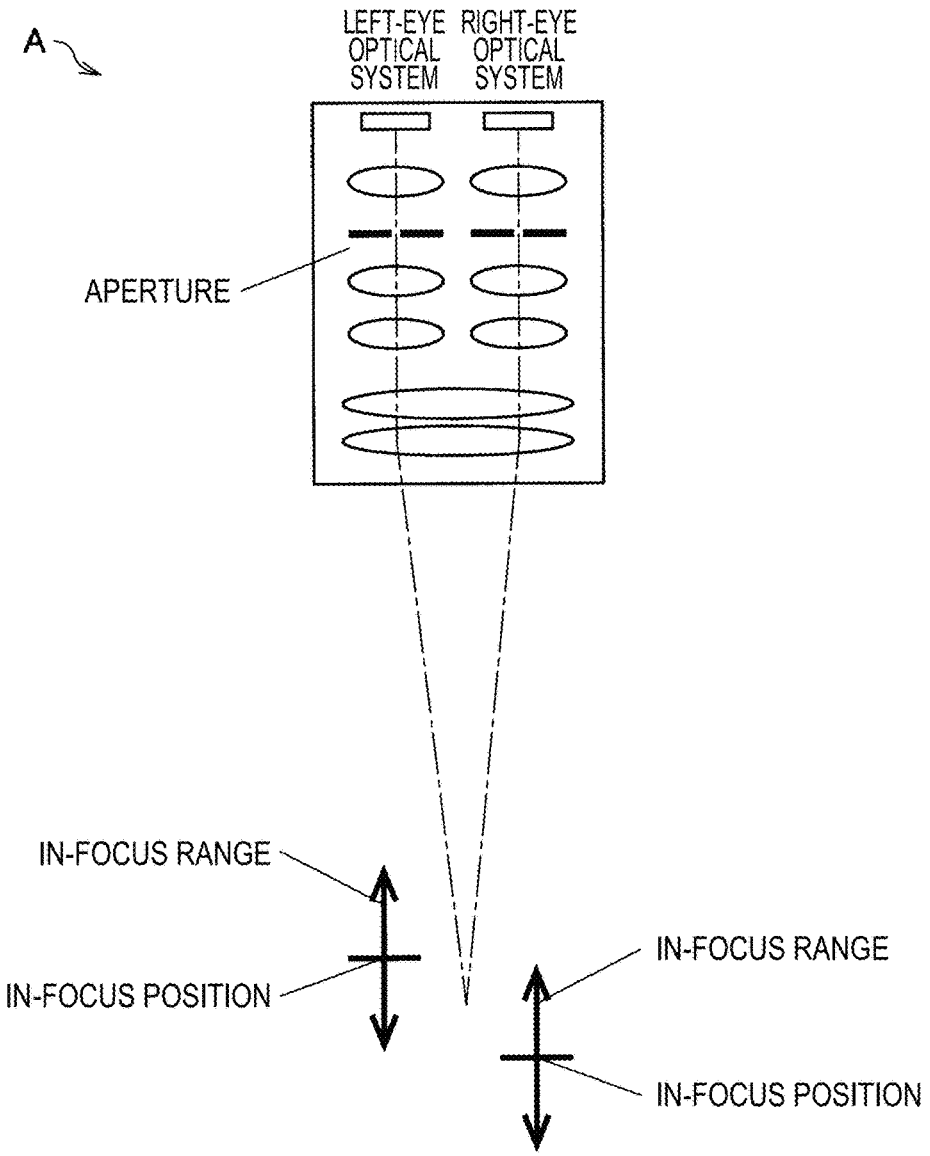
FIG. 4 is an explanatory diagram illustrating one example of an imaging device that functions as a stereo camera.

FIG. 2 is an explanatory diagram for explaining an example of the configuration of the imaging device 106 provided in the medical observation apparatus 100 according to the present embodiment.

For example, the imaging device 106 includes an imaging member 120 and a barrel member 122 having an approximately cylindrical shape, with the imaging member 120 being provided inside the barrel member 122.

On an aperture on the bottom end of the barrel member 122 (the lower end in FIG. 2), for example, a cover glass (not illustrated) for protecting the imaging member 120 is provided.

Additionally, for example, a light source (not illustrated) is provided inside the barrel member 122, and during imaging, the subject is irradiated with illuminating light radiating from the light source through the cover glass. Reflected light (observation light) from the subject irradiated with illuminating light enters the imaging member 120 through the cover glass (not illustrated), whereby an image signal indicating the subject (an image signal indicating a medical captured image) is obtained by the imaging member 120.

As the imaging member 120, any of various known types of configurations used in an electronic imaging microscope section can be applied.

To give one example, the imaging member 120 includes an optical system 120a and an image sensor 120b including an imaging element that takes an image of an observation target with light transmitted through the optical system 120a, for example. The optical system 120a includes optical elements such as a mirror and one or multiple lenses, such as an objective lens, a zoom lens, and a focus lens, for example. Examples of the image sensor 120b include an image sensor using multiple imaging elements, such as a complementary metal-oxide semiconductor (CMOS) or a charge-coupled device (CCD).

The imaging member 120, by including two or more imaging devices provided with an optical system 120a and an image sensor 120b, for example, functions as what is called a stereo camera. In the configuration of the imaging device 106 that functions as a stereo camera, the optical system may be a Galileo optical system or a Greenough optical system.

Figure 5:
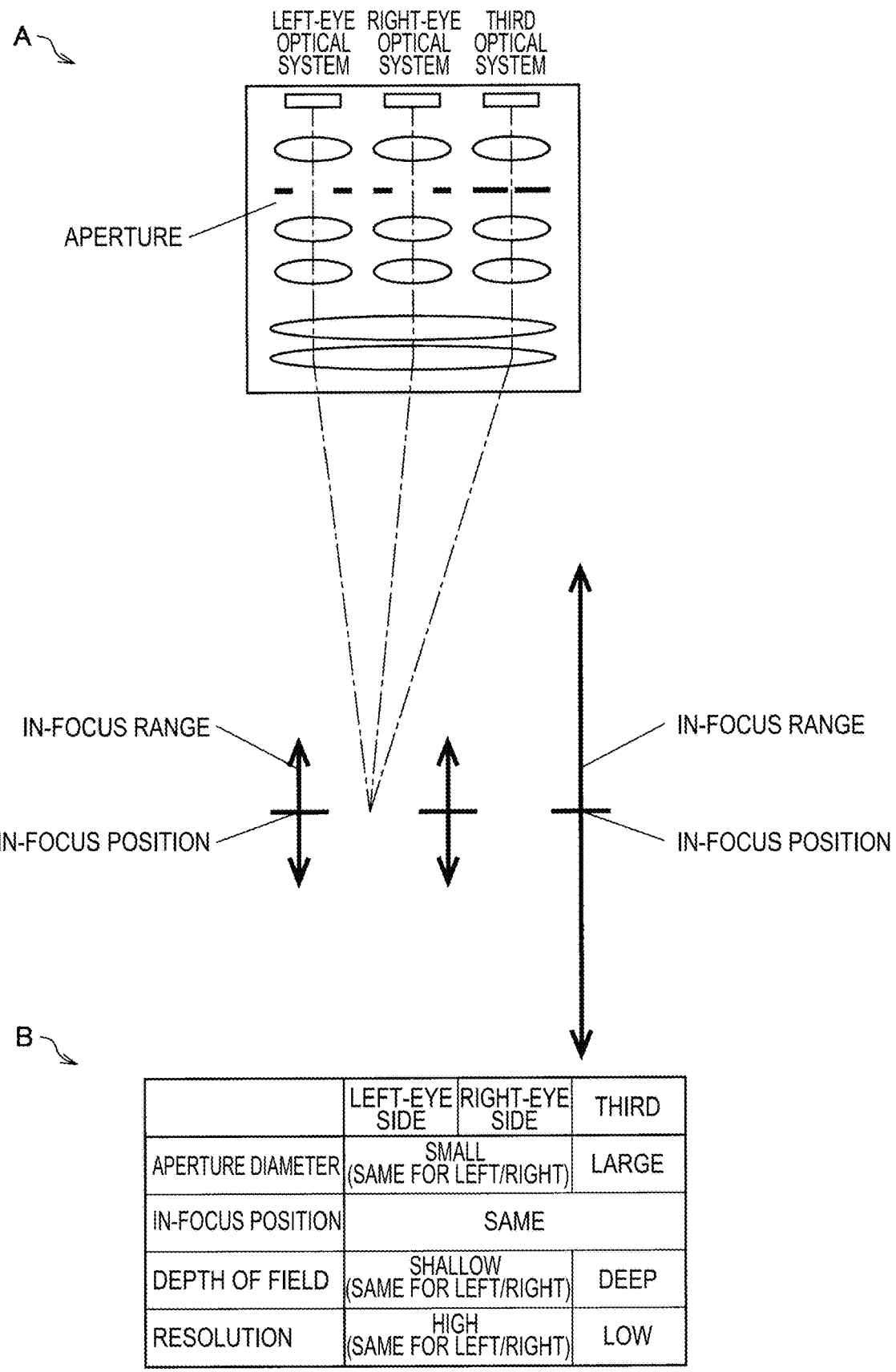
FIG. 5 is an explanatory diagram illustrating one example of an imaging device that functions as a stereo camera.
Figure 6:
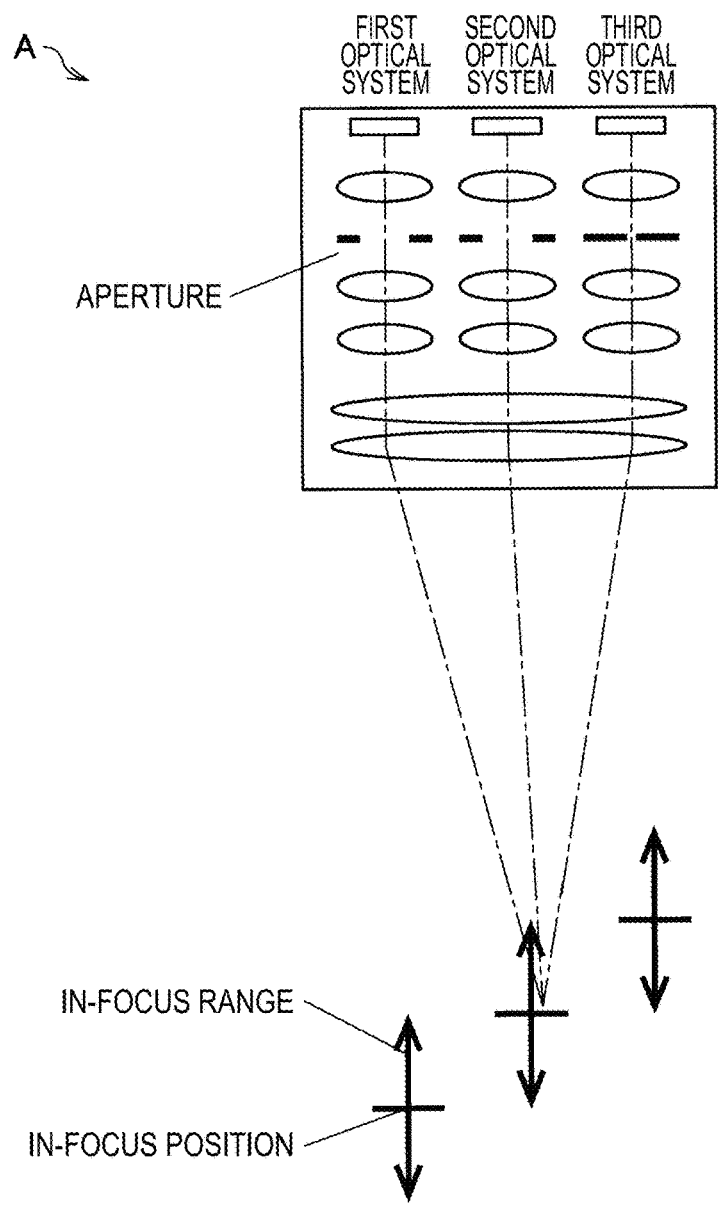
FIG. 6 is an explanatory diagram illustrating one example of an imaging device that functions as a stereo camera.

FIGS. 3 to 6 are explanatory diagrams illustrating examples of imaging devices that function as a stereo camera. Each of A in FIG. 3, A in FIG. 4, A in FIG. 5, and A in FIG. 6 illustrates an example of an optical system provided in an imaging device that functions as a stereo camera, and illustrates an example in which the optical system is a Galileo optical system. Each of B in FIG. 3, B in FIG. 4, B in FIG. 5, and B in FIG. 6 expresses the characteristics in each corresponding diagram in table format. The following gives an example of a case in which the medical observation apparatus 100 according to the present embodiment, including the medical observation apparatus 100 included in the medical observation system according to the second example described later, is provided with multiple imaging devices in a configuration having a Galileo optical system as illustrated in FIGS. 3 to 6, and multiple medical captured images, including a medical captured image for the right eye and a medical captured image for the left eye, are obtained. Also, the following gives an example of a case in which, as illustrated in FIGS. 3 to 6, the multiple imaging devices include imaging devices in which one or both of the in-focus position and the in-focus range are different. Note that the configuration provided with multiple imaging devices obviously is not limited to a configuration having a Galileo optical system as illustrated in FIGS. 3 to 6.

Each imaging device included in the imaging member 120 is equipped with one or multiple functions typically provided in an electronic imaging microscope section, such as a zoom function (one or both of an optical zoom function and an electronic zoom function) and an autofocus (AF) function.

In addition, the imaging member 120 may also be configured to be capable of imaging at what are called high resolutions, such as 4K and 8K, for example. By configuring the imaging member 120 to be capable of imaging at high resolutions, it becomes possible to ensure a predetermined resolution (such as full HD image quality, for example), while also displaying an image on the display apparatus 200 having a large display screen, such as 50 inches or more, for example. For this reason, visibility is improved for the surgeon watching the display screen. Also, by configuring the imaging member 120 to be capable of imaging at high resolutions, even if the captured image is enlarged by the electronic zoom function and displayed on the display screen of the display apparatus 200, it is still possible to ensure a predetermined resolution. Furthermore, in the case of using the electronic zoom function to ensure a predetermined resolution, since it is possible to reduce the performance of the optical zoom function in the imaging device 106, the optical system of the imaging device 106 can be simplified, and the imaging device 106 can be configured more compactly.

In the imaging device 106, for example, various operating devices for controlling the operation of the imaging device 106 are provided. For example, in FIG. 2, a zoom switch 124, a focus switch 126, and an operating mode change switch 128 are provided on the imaging device 106. Note that the positions and shapes in which to provide the zoom switch 124, the focus switch 126, and the operating mode change switch 128 obviously are not limited to the example illustrated in FIG. 2. The zoom switch 124 and the focus switch 126 are an example of an operating device for adjusting the imaging parameters in the imaging device 106.

The zoom switch 124 includes, for example, a zoom-in switch 124a that increases the zoom magnification (enlargement ratio), and a zoom-out switch 124b that decreases the zoom magnification. By performing an operation on the zoom switch 124, the zoom magnification is adjusted, and the zoom is adjusted.

The focus switch 126 includes, for example, a long-range focus switch 126a that increases the focal length to the observation target (subject), and a close-range focus switch 126b that decreases the focal length to the observation target. By performing an operation on the focus switch 126, the focal length is adjusted, and the focus is adjusted.

The operating mode change switch 128 is an example of an operating device for changing the operating mode of the arm 104 in the imaging device 106. By performing an operation on the operating mode change switch 128, the operating mode of the arm 104 is changed. Examples of operating modes of the arm 104 include a locked mode and a free mode, as described above.

One example of an operation with respect to the operating mode change switch 128 is an operation of pressing the operating mode change switch 128. For example, the operating mode of the arm 104 becomes the free mode while the surgeon is pressing the operating mode change switch 128, and the operating mode of the arm 104 becomes the locked mode when the surgeon is not pressing the operating mode change switch 128.

In addition, the imaging device 106 is provided with, for example, an anti-slip member 130 and a projecting member 132 in order to further raise operability, convenience, and the like when an operator who performs operations on various operation devices performs an operation.

The anti-slip member 130 is a member provided to prevent slipping of an operating body such as a hand when, for example, the operator performs an operation on the barrel member 122 with the operating body. The anti-slip member 130 is formed with a material having a large coefficient of friction, for example, and has a slip-resistant structure due to unevenness or the like.

The projecting member 132 is member provided to prevent an operating body such as a hand blocking the field of view of the optical system 120a when the operator performs an operation on the barrel member 122 with the operating body, or to prevent a cover glass (not illustrated) from becoming dirty due to the cover glass being contacted by the operating body when an operation is performed with the operating body.

Note that the position and shape in which each of the anti-slip member 130 and the projecting member 132 is provided obviously are not limited to the example illustrated in FIG. 2. In addition, the imaging device 106 does not have to be provided with one or both of the anti-slip member 130 and the projecting member 132.

The image signal (image data) generated by imaging in the imaging device 106 is subjected to image processing in a processor that functions as the control section described later, for example. Examples of image processing according to the present embodiment include one or multiple processes from among various processes such as gamma correction, white balance adjustment, image enlargement or reduction related to the electronic zoom function, and pixel interpolation, for example. Also, the image processing according to the present embodiment may include the processes related to the image processing method described later, for example.

Note that in the case in which the medical observation system according to the present embodiment includes a medical control apparatus (not illustrated) that controls various operations in the medical observation apparatus 100, the image processing according to the present embodiment may also be performed in the medical control apparatus (not illustrated). In this case, the medical control apparatus (not illustrated) functions as a medical image processing apparatus capable of executing the processes related to the image processing method according to the present embodiment.

For example, the medical observation apparatus 100 transmits a display control signal and the image signal subjected to image processing as described above to the display apparatus 200.

By transmitting the display control signal and the image signal to the display apparatus 200, on the display screen of the display apparatus 200, a medical captured image in which the observation target is imaged (for example, a captured image in which the operating site is imaged) is displayed enlarged or reduced at a desired magnification by one or both of the optical zoom function and the electronic zoom function.

The medical observation apparatus 100 illustrated in FIG. 1 includes the hardware configuration illustrated with reference to FIGS. 1 and 2, for example.

Note that the hardware configuration of the medical observation apparatus according to the present embodiment is not limited to the configuration illustrated with reference to FIGS. 1 and 2.

For example, the medical observation apparatus according to the present embodiment may also be a configuration not provided with the base 102, in which the arm 104 is directly attached to the ceiling, a wall, or the like of the operating room or the like. For example, in the case in which the arm 104 is attached to the ceiling, the medical observation apparatus according to the present embodiment becomes a configuration in which the arm 104 hangs down from the ceiling.

Also, although FIG. 1 illustrates an example in which the arm 104 is configured so that six degrees of freedom are realized with respect to the driving of the imaging device 106, the configuration of the arm 104 is not limited to a configuration whereby the degrees of freedom with respect to the driving of the imaging device 106 become six degrees of freedom. For example, it is sufficient to configure the arm 104 so that the imaging device 106 can move appropriately in accordance with the application, and factors such as the number and arrangement of joint sections and links, and the directions of the drive shafts of the joint sections can be set appropriately so that the arm 104 has the desired degrees of freedom.

Also, although FIGS. 1 and 2 illustrate an example in which various types of operating devices for controlling the operation of the imaging device 106 are provided on the imaging device 106, some or all of the operating devices illustrated in FIGS. 1 and 2 may also not be provided on the imaging device 106. To give one example, the various types of operating devices for controlling the operation of the imaging device 106 may also be provided in another part other than the imaging device 106 included in the medical observation apparatus according to the present embodiment. Also, to give another example, the various types of operating devices for controlling the operation of the imaging device 106 may also be external operating devices, such as a footswitch or a remote controller.

Additionally, the imaging device 106 may also have a configuration enabling switching among multiple observation modes. Observation modes according to the present embodiment may include, for example, an observation mode that executes imaging with natural light, an observation mode that executes imaging with special light, an observation mode that executes imaging by utilizing an image-enhancing observation technology such as narrow-band imaging (NBI), and the like. Special light according to the present embodiment refers to light in a specific wavelength band, such as light in the fluorescent wavelength band of fluorescent observation using 5-Aminolevulinic acid (5-ALA).

One example of the configuration of the imaging device 106 enabling switching among multiple observation modes is a "configuration provided with a filter that allows light of a specific wavelength band to pass through while not allowing light of other wavelength bands to pass through, and a movement mechanism that selectively disposes the filter on the optical path", for example. The specific wavelength band that the filter according to the present embodiment allows to pass through may be, for example, the wavelength band of near-infrared rays (for example, the wavelength band from approximately 0.7 [micrometers] to 2.5 [micrometers]), the fluorescent wavelength band for fluorescent observation using 5-ALA (for example, the wavelength band from approximately 0.6 [micrometers] to 0.65 [micrometers]), the fluorescent wavelength band of indocyanine green (ICG) (for example, the wavelength band from approximately 0.82 [micrometers] to 0.85 [micrometers]), or the like.

Note that the imaging device 106 may also be provided with multiple filters that allow different wavelength bands to pass through. Also, although the above illustrates an example in which imaging is executed with the light of a specific wavelength band by disposing a filter on the optical path, the configuration of the imaging device 106 for executing imaging with the light of a specific wavelength band obviously is not limited to the example illustrated above.

[1-2] Medical Observation System According to Second Example

The medical observation system 1000 according to the present embodiment is not limited to the configuration illustrated in the first example illustrated in FIG. 1. Next, as another example of the medical observation system 1000, one example of a configuration of the medical observation system 1000 including the medical observation apparatus 100 that functions as an endoscopic apparatus will be described.

Figure 7:
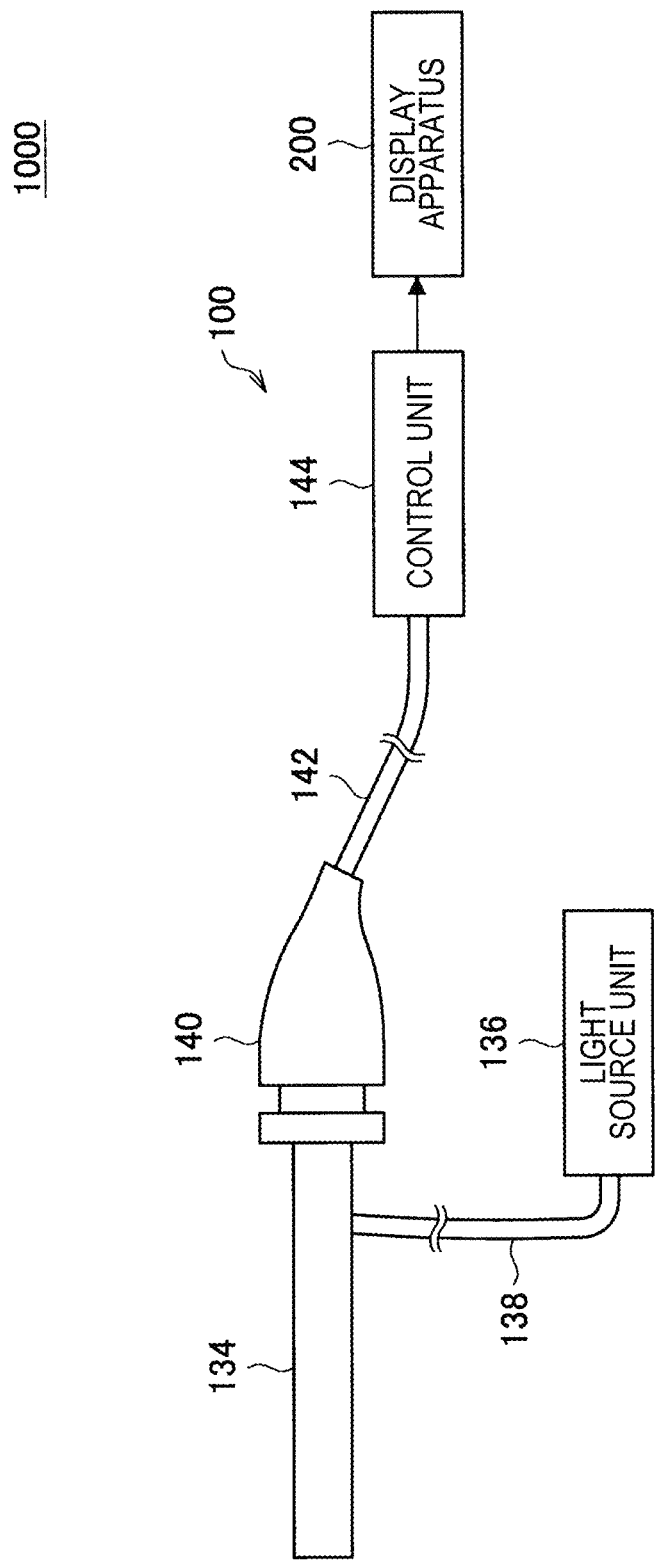
FIG. 7 is an explanatory diagram illustrating a second example of a configuration of a medical observation system according to the present embodiment.

FIG. 7 is an explanatory diagram illustrating a second example of the configuration of the medical observation system 1000 according to the present embodiment. The medical observation system 1000 illustrated in FIG. 7 includes the medical observation apparatus 100 and the display apparatus 200, for example. In the case in which the medical observation apparatus 100 illustrated in FIG. 7 is used during surgery, the surgeon observes the surgical site while referring to a medical captured image captured by the medical observation apparatus 100 and displayed on the display screen of the display apparatus 200, and performs various treatments, such as techniques depending on the surgical procedure, on the surgical site.

Note that the medical observation system according to the second example is not limited to the example illustrated in FIG. 7.

For example, the medical observation system according to the second example additionally may include a medical control apparatus (not illustrated) that controls various operations in the medical observation apparatus 100, similarly to the medical observation system according to the first example.

Also, the medical observation system according to the second example may be a configuration including a plurality of one or both of the medical observation apparatus 100 and the display apparatus 200, similarly to the medical observation system according to the first example.

Hereinafter, each apparatus included in the medical observation system 1000 according to the second example illustrated in FIG. 7 will be described.

[1-2-1] Display Apparatus 200

The display apparatus 200 is a display device in the medical observation system 1000 according to the second example, and corresponds to an external display device from the perspective of the medical observation apparatus 100. The display apparatus 200 included in the medical observation system 1000 according to the second example is similar to the display apparatus 200 included in the medical observation system 1000 according to the first example.

[1-2-2] Medical Observation Apparatus 100

The medical observation apparatus 100 illustrated in FIG. 7 is provided with an insertion member 134, a light source unit 136, a light guide 138, a camera head 140, a cable 142, and a control unit 144, for example. The medical observation apparatus 100 runs on electric power supplied from an internal power source such as a battery provided in the medical observation apparatus 100, on electric power supplied from a connected external power source, or the like, for example.

The insertion member 134 has an elongated shape, and is internally provided with an optical system that condenses incident light. The front end of the insertion member 134 is inserted inside a body cavity of a patient. The rear end of the insertion member 134 is detachably connected to the front end of the camera head 140. Also, the insertion member 134 is connected to the light source unit 136 through the light guide 138, and is supplied with light from the light source unit 136.

The insertion member 134 may be formed with an inflexible material or a flexible material. Depending on the material used to form the insertion member 134, the medical observation apparatus 100 may be called a rigid scope or a flexible scope.

The light source unit 136 is connected to the insertion member 134 through the light guide 138. The light source unit 136 supplies light to the insertion member 134 through the light guide 138.

For example, the light source unit 136 includes multiple light sources that emit light of different wavelengths. The multiple light sources included in the light source unit 136 may be, for example, a light source that emits red light, a light source that emits green light, and a light source that emits blue light. The light source that emits red light may be one or multiple red light-emitting diodes, for example. The light source that emits green light may be one or multiple green light-emitting diodes, for example. The light source that emits blue light may be one or multiple blue light-emitting diodes, for example. Note that the multiple light sources included in the light source unit 136 obviously are not limited to the example illustrated above. For example, the light source unit 136 includes the multiple light sources on a single chip or includes the multiple light sources on multiple chips.

The light source unit 136 is connected to the control unit 144 in a wired or wireless manner, and the light emission in the light source unit 136 is controlled by the control unit 144.

Light supplied to the insertion member 134 is emitted from the front end of the insertion member 134, and irradiates an observation target such as tissue inside the body cavity of the patient. Additionally, reflected light from the observation target is condensed by the optical system inside the insertion member 134.

The camera head 140 has a function of imaging the observation target. The camera head 140 is connected to the control unit 144 through a signal transmission member, namely the cable 142.

The camera head 140 includes an image sensor, images the observation target by photoelectrically converting the reflected light from the observation target condensed by the insertion member 134, and outputs an image signal obtained by the imaging (a signal expressing the medical captured image) to the control unit 144 through the cable 142. The image sensor included in the camera head 140 may be, for example, an image sensor using multiple imaging elements such as CMOS and CCD elements.

In the medical observation apparatus 100 that functions as an endoscopic apparatus, for example, the insertion member 134, the light source unit 136, and the camera head 140 fulfill the role of an "imaging device that is inserted inside a body of a patient and images the inside of the body".

Note that the medical observation apparatus 100 that functions as an endoscopic apparatus may also be a configuration provided with multiple imaging devices that function as what is called a stereo camera, for example. In a configuration of imaging devices that function as a stereo camera, similarly to the medical observation apparatus 100 included in the medical observation system according to the first example, the optical system may be a Galileo optical system or a Greenough optical system.

The control unit 144 controls the imaging device. More specifically, the control unit 144 controls each of the light source unit 136 and the camera head 140.

Also, the control unit 144 includes a communication device (not illustrated), and transmits an image signal output from the camera head 140 to the display apparatus 200 by any form of wireless communication or any form of wired communication. The control unit 144 may also transmit an image signal and a display control signal to the display apparatus 200.

The communication device (not illustrated) included in the control unit 144 may be, for example, an IEEE 802.15.1 port and a transmitting-receiving circuit (wireless communication), an IEEE 802.11 port and a transmitting-receiving circuit (wireless communication), a communication antenna and an RF circuit (wireless communication), an optical communication device (wireless communication or wired communication), a LAN terminal and a transmitting-receiving circuit (wired communication), or the like. The communication device (not illustrated) may also be a configuration capable of communicating with one or multiple external apparatus by multiple communication methods.

In addition, the control unit 144 may execute predetermined processing on the image signal output from the camera head 140, and transmit the image signal that has been subjected to the predetermined processing to the display apparatus 200. The predetermined processing on the image signal may be, for example, white balance adjustment, image enlargement or reduction according to an electronic zoom function, pixel interpolation, and the like. Additionally, the predetermined processing on the image signal may also include the processes related to the image processing method described later, for example.

Note that the control unit 144 may also store a medical captured image based on the image signal.

The control unit 144 may be a camera control unit (CCU), for example.

The medical observation apparatus 100 that functions as an endoscopic apparatus includes the hardware configuration illustrated with reference to FIG. 7, for example. In the medical observation apparatus 100 that functions as an endoscopic apparatus, for example, the insertion member 134, the light source unit 136, and the camera head 140 fulfill the role of the imaging device, and imaging in the imaging device is controlled by the control unit 144.

[1-3] Medical Observation System According to Other Example

The medical observation system according to the present embodiment is not limited to the configuration illustrated by the first example illustrated in FIG. 1 or the configuration illustrated by the second example illustrated in FIG. 7. For example, the medical observation apparatus included in the medical observation system according to the present embodiment may also be a configuration in which multiple imaging devices are provided with respect to an optical medical observation apparatus. Even in an optical medical observation apparatus provided with multiple imaging devices, it is possible to apply the image processing method described later. The following gives an example of a case in which the medical observation apparatus included in the medical observation system according to the present embodiment is the medical observation apparatus 100 illustrated in FIGS. 1 and 7.

[1-4] Functional Configuration of Medical Observation Apparatus

Figure 8:
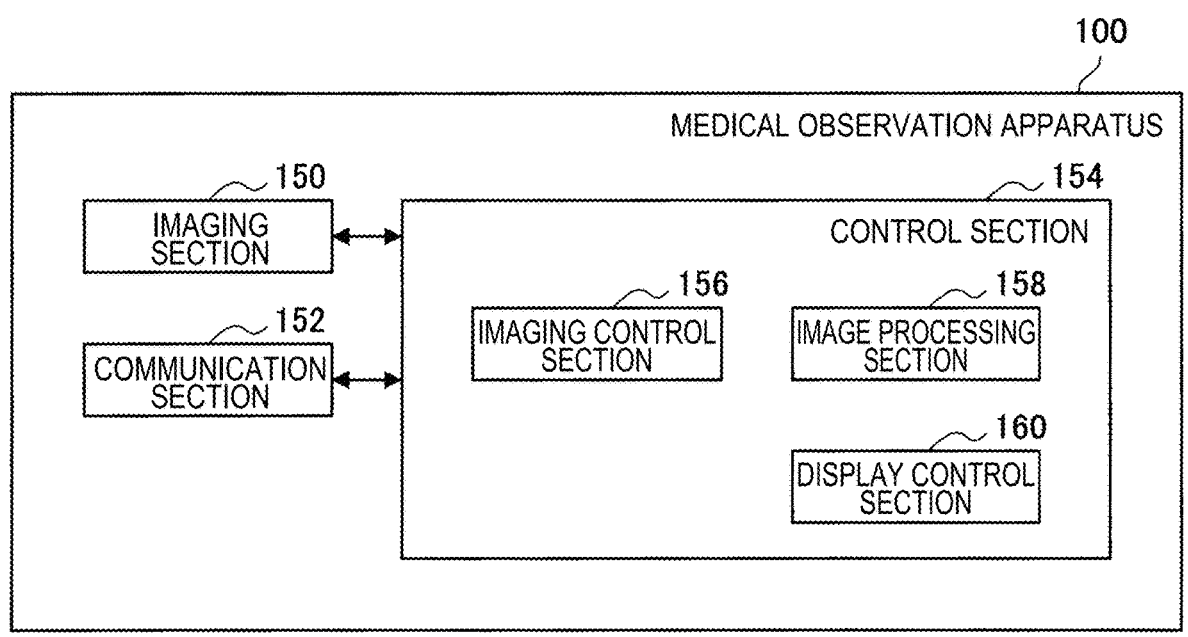
FIG. 8 is a function block diagram illustrating one example of a configuration of a medical observation apparatus according to the present embodiment.

Next, the medical observation apparatus 100 illustrated in FIGS. 1 and 7 will be described using function blocks. FIG. 8 is a function block diagram illustrating one example of the configuration of the medical observation apparatus 100 according to the present embodiment.

For example, the medical observation apparatus 100 is provided with an imaging section 150, a communication section 152, and a control section 154.

The imaging section 150 images the observation target. For example, the imaging section 150 includes the "imaging device 106" (in the case of the medical observation apparatus 100 illustrated in FIG. 1), or the "insertion member 134, the light source unit 136, and the camera head 140" (in the case of the medical observation apparatus 100 illustrated in FIG. 7). Imaging in the imaging section 150 is controlled by the control section 154, for example.

The communication section 152 is a communication device provided in the medical observation apparatus 100, and fulfills a role of communicating in a wireless or wired manner with an external apparatus such as the display apparatus 200. The communication section 152 includes the communication device (not illustrated) described above, for example. Communication in the communication section 152 is controlled by the control section 154, for example.

The control section 154 includes the processor (not illustrated) described above, for example, and fulfills a role of controlling the medical observation apparatus 100 overall. In addition, the control section 154 fulfills a role of leading the execution of the processes related to the image processing method described later. Note that the processes related to the image processing method in the control section 154 may also be executed in a distributed manner by multiple processing circuits (such as multiple processors, for example).

More specifically, the control section 154 includes an imaging control section 156, an image processing section 158, and a display control section 160, for example.

The imaging control section 156 controls the imaging device included in the imaging section 150. Examples of the control of the imaging device include control of one or multiple functions typically provided in an electronic imaging microscope section, such as control of an AF function, including at least a zoom function (one or both of an optical zoom function and an electronic zoom function).

The image processing section 158 executes the processes related to the image processing method according to the present embodiment on multiple medical captured images in which the observation target is imaged by each of multiple imaging devices. One example of the processes related to the image processing method according to the present embodiment will be described later.

For example, the display control section 160 controls the display on the display apparatus 200 by conveying the display control signal and the image signal to the communication device (not illustrated) included in the communication section 152, and causing the display control signal and the image signal to be transmitted to the display apparatus 200. The image signal that the display control section 160 causes to be transmitted may include an image signal after the processes related to the image processing method are executed in the image processing section 158. Note that the control of communication in the communication section 152 may also be performed by a communication control section (not illustrated) included in the control section 154.

For example, by including the image processing section 158, the control section 154 fulfills a role of leading the execution of the processes related to the image processing method according to the present embodiment. Also, for example, by including the imaging control section 156 and the display control section 160, the control section 154 fulfills a role of controlling the medical observation apparatus 100 overall.

Note that the functional configuration of the control section 154 is not limited to the example illustrated in FIG. 8.

For example, it is possible for the control section 154 to have any configuration corresponding to how the functions included in the medical observation apparatus 100 are divided up, such as a configuration corresponding to how the processes related to the image processing method according to the present embodiment are divided up.

To give one example, in the case in which the medical observation apparatus 100 has the configuration illustrated in FIG. 1, the control section 154 additionally may include an arm control section (not illustrated) that controls the driving of the arm 104. One example of control of the driving of the arm 104 includes, for example, "applying a control signal that controls driving to the actuators (not illustrated) corresponding to each of the joint sections 110a, 110b, 110c, 110d, 110e, and 110f", and the like.

The medical observation apparatus 100 performs processes related to the image processing method according to the present embodiment described later with the functional configuration illustrated in FIG. 8, for example.

Note that the functional configuration of the medical observation apparatus according to the present embodiment is not limited to the configuration illustrated in FIG. 8.

For example, in the medical observation apparatus according to the present embodiment, some or all of the imaging control section 156, the image processing section 158, and the display control section 160 illustrated in FIG. 8 can be provided separately from the control section 154 (for example, realized by a different processing circuit).

Additionally, in the medical observation apparatus according to the present embodiment, the functional configuration capable of executing the processes related to the image processing method according to the present embodiment is not limited to the configuration illustrated in FIG. 8, and it is possible for the medical observation apparatus according to the present embodiment to take a functional configuration corresponding to how the processes related to the image processing method according to the present embodiment are divided up.

Also, in the case in which the medical observation apparatus according to the present embodiment has the configuration illustrated in FIG. 1, the medical observation apparatus according to the present embodiment includes an arm section (not illustrated) including the arm 104. The arm 104 included in the arm section (not illustrated) supports the imaging device 106 included in the imaging section 150.

Also, for example, in the case of communicating with an external apparatus via an external communication device having a function and configuration similar to the communication section 152, the medical observation apparatus according to the present embodiment may also not be provided with the communication section 152.

Also, in the case in which the medical observation system according to the present embodiment includes a medical control apparatus (not illustrated), and the medical observation apparatus according to the present embodiment is controlled by the medical control apparatus (not illustrated), the medical observation apparatus according to the present embodiment may also not be provided with the control section 154.

Herein, the medical control apparatus (not illustrated) is, for example, provided with a control section having a function and configuration similar to the control section 154, and thereby executes processes related to the image processing method according to the present embodiment described later, and in addition, controls the operation in each structural element such as the imaging section 150 provided in the medical observation apparatus according to the present embodiment. The medical control apparatus (not illustrated) communicates with the medical observation apparatus according to the present embodiment via a provided communication device or a connected external communication device, and thereby controls the operation in each structural element provided in the medical observation apparatus according to the present embodiment.

Furthermore, in the case in which the medical observation system according to the present embodiment includes the medical control apparatus (not illustrated), and the medical observation apparatus according to the present embodiment is controlled by the medical control apparatus (not illustrated), it is also possible for the medical observation apparatus according to the present embodiment to take a configuration that does not include some of the functions of the control section 154.

[2] Image Processing Method According to Present Embodiment

Next, the image processing method according to the present embodiment will be described. The following gives an example of a case in which the processes related to the image processing method according to the present embodiment are executed by the medical observation apparatus 100 (more specifically, the image processing section 158 of the control section 154 included in the medical observation apparatus 100, for example). Note that, as described above, in the medical observation system according to the present embodiment, the processes related to the image processing method according to the present embodiment may also be executed by the display apparatus 200, a medical control apparatus (not illustrated), or the like.

[2-1] Processes Related to Image Processing Method According to Present Embodiment As methods of potentially achieving both a deeper depth of field and a higher resolution, the first method and the other method described above are conceivable. However, the first method described above leads to bulkier equipment. Also, with the other method described above, there is a possibility that the observer will experience strain, and in addition, since the other method described above is not a method of processing the captured images, the method is not desirable from the perspective of saving and utilizing the captured images.

Accordingly, the medical observation apparatus 100 potentially achieves both a deeper depth of field and a higher resolution by processing multiple medical captured images in which the observation target is imaged by each of "multiple imaging devices including imaging devices in which one or both of the in-focus position and the in-focus range are different, like the configurations illustrated in FIGS. 3 to 6, for example". More specifically, the medical observation apparatus 100 potentially achieves both a deeper depth of field and a higher resolution by executing a "depth compositing process that complements each of the medical captured image for the right eye and the medical captured image for the left eye among the multiple medical captured images with an other medical captured image, and expands the depth of field of each medical captured image".

At this point, in the case of attempting to complement each of the medical captured image for the right eye and the medical captured image for the left eye with an other medical captured image, the parallax between the multiple imaging devices means that even if the same observation target is imaged, the multiple medical captured images will not be the same images.

For this reason, the medical observation apparatus 100 associates the multiple medical captured images (association process).

For example, the medical observation apparatus 100 associates the multiple medical captured images by extracting a characteristic portion from each of the multiple medical captured images and matching the extracted characteristic portions. The characteristic portion in a medical captured image is extracted by using any technology capable of extracting a characteristic portion from an image, such as one or both of edges detected by any edge detection process and the result of any perimeter survey process, for example. Also, the medical observation apparatus 100 associates the multiple medical captured images by using any technology capable of comparing extracted characteristic portions to identify the same subject, such as pattern matching, for example.

Additionally, the medical observation apparatus 100 may also associate the multiple medical captured images by estimating the same subject included in each of the multiple medical captured images on the basis of settings information indicating the settings of each of the multiple imaging devices, for example.

The settings information according to the present embodiment may be data indicating any parameters enabling control of the imaging in the imaging device, such as the focal length and the angle of view, for example. In addition, the settings information according to the present embodiment may also include data indicating a baseline length between the multiple imaging devices.

In the case of imaging the observation target with multiple imaging devices, since it is possible to specify from the settings information the conditions under which each imaging device is imaging the observation target, it is possible to estimate a region where the subject is included in each of the multiple medical captured images. The medical observation apparatus 100 associates the multiple medical captured images by using any technology capable of comparing estimated regions to identify the same subject, such as pattern matching, for example.

Note that examples of the association process according to the present embodiment are not limited to the examples illustrated above, and the medical observation apparatus 100 may associate the multiple medical captured images by using any technology capable of comparing and associating multiple images.

When the multiple medical captured images are associated, the medical observation apparatus 100 depth-composites each of the medical captured image for the right eye and the medical captured image for the left eye among the multiple medical captured images using the associated other medical captured image (compositing process). The medical observation apparatus 100 performs depth compositing by complementing each of the medical captured image for the right eye and the medical captured image for the left eye with the other medical captured image of higher resolution. By complementing each of the medical captured image for the right eye and the medical captured image for the left eye with the other medical captured image of higher resolution, the depth of field of each medical captured image is expanded. A specific example of the compositing process according to the present embodiment will be described later.

By executing the processes related to the image processing method according to the present embodiment, each of the medical captured image for the right eye and the medical captured image for the left eye becomes a medical captured image complemented by an other medical captured image of higher resolution. Therefore, by executing the processes related to the image processing method according to the present embodiment, both a deeper depth of field and a higher resolution can be potentially achieved in each of the medical captured image for the right eye and the medical captured image for the left eye.

[2-2] Example of Processes Related to Image Processing Method According to Present Embodiment Next, an example of the processes related to the image processing method according to the present embodiment will be illustrated.

(1) First Example of Processes Related to Image Processing Method

First, as a first example of the processes related to the image processing method, an example of the processes related to the image processing method in the "case in which the multiple imaging devices are the two imaging devices of an imaging device that captures a medical captured image for the right eye and an imaging device that captures a medical captured image for the left eye" will be described. For example, in the two imaging devices, the in-focus range is different like in the example illustrated in FIG. 3, the in-focus position is different like in the example illustrated in FIG. 4, or both the in-focus position and the in-focus range are different.

Figure 9:
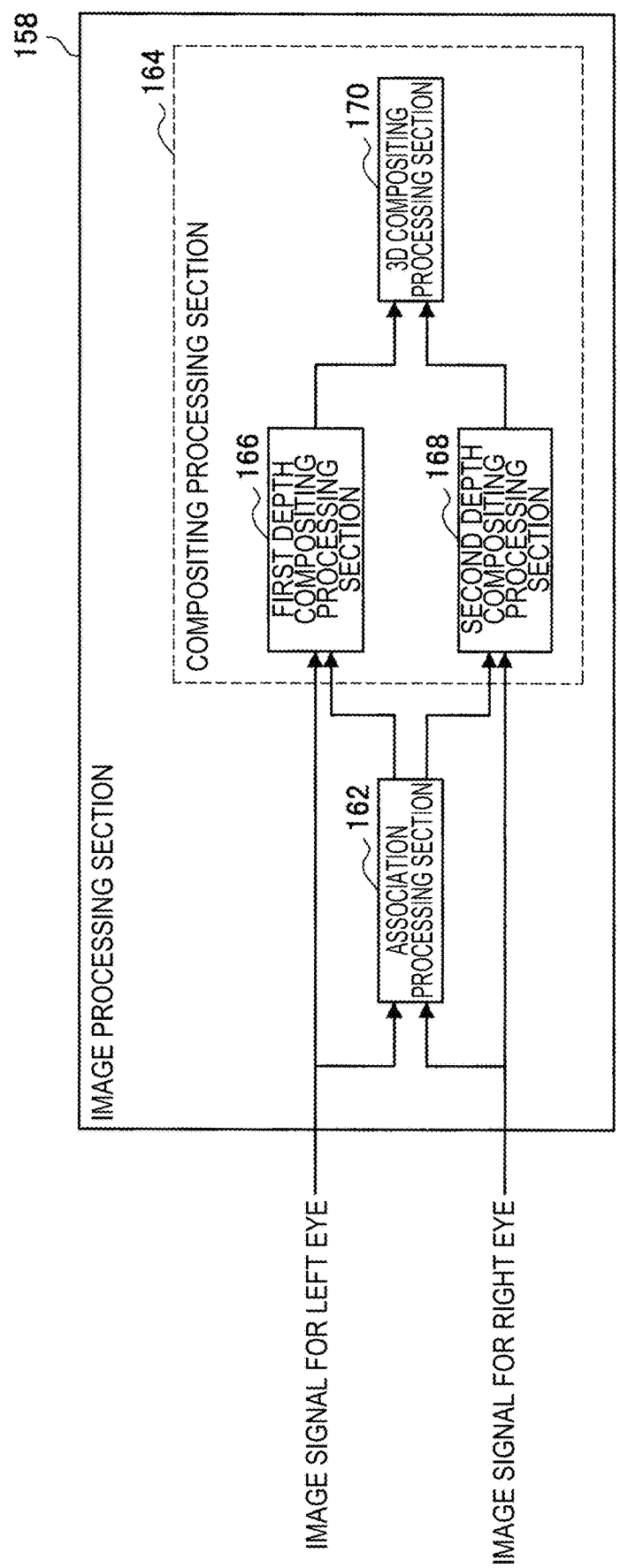
FIG. 9 is an explanatory diagram for explaining one example of processes related to the image processing method according to the present embodiment.

FIG. 9 is an explanatory diagram for explaining one example of the processes related to the image processing method according to the present embodiment, and illustrates processes in the image processing section 158 illustrated in FIG. 8 as function blocks.

The image processing section 158 includes an association processing section 162 and a compositing processing section 164.

The association processing section 162 fulfills a role of executing the association process according to the present embodiment, and associates the medical captured image for the right eye and the medical captured image for the left eye. For example, the association processing section 162 associates the medical captured image for the right eye and the medical captured image for the left eye by using any technology capable of comparing and associating multiple images, such as a process of extracting and matching characteristic portions from each of multiple medical captured images.

For example, the association processing section 162 conveys a result of associating the medical captured image for the left eye with the medical captured image for the right eye and a result of associating the medical captured image for the right eye with the medical captured image for the left eye to the compositing processing section 164. For example, the result of associating the medical captured image for the left eye with the medical captured image for the right eye may be an image signal expressing the associated medical captured image for the left eye, or data indicating a region matched with the medical captured image for the right eye in the medical captured image for the left eye. Also, the result of associating the medical captured image for the right eye with the medical captured image for the left eye may be an image signal expressing the associated medical captured image for the right eye, or data indicating a region matched with the medical captured image for the left eye in the medical captured image for the right eye. Note that the association result according to the present embodiment is not limited to the examples illustrated above, and sufficiently is data in any format capable of specifying an association relationship between multiple medical captured images.

The compositing processing section 164 includes a first depth compositing processing section 166, a second depth compositing processing section 168, and a 3D compositing processing section 170, for example. In the compositing processing section 164, the first depth compositing processing section 166 and the second depth compositing processing section 168 fulfill a role of executing the compositing process related to the image processing method according to the present embodiment.

The first depth compositing processing section 166 depth-composites the medical captured image for the left eye using the associated medical captured image for the right eye (one example of an other medical captured image).

Figure 10:
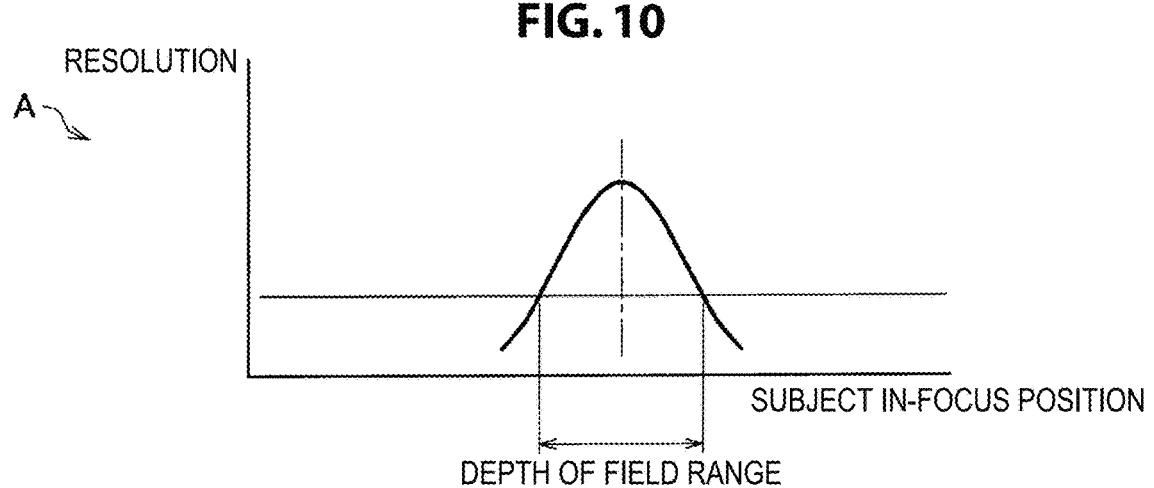
FIG. 10 is an explanatory diagram for explaining one example of a depth compositing process related to the image processing method according to the present embodiment.
Figure 10:
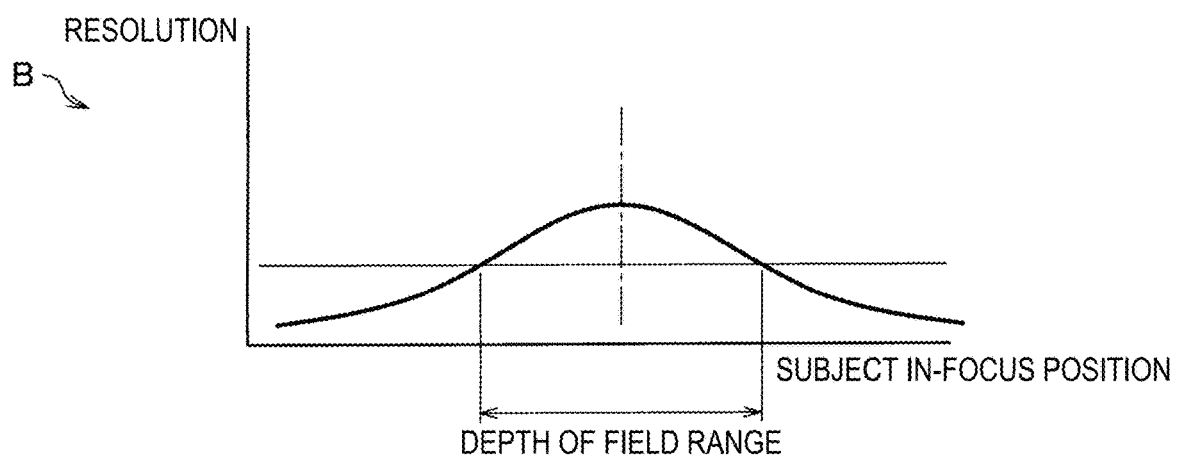
Figure 10:
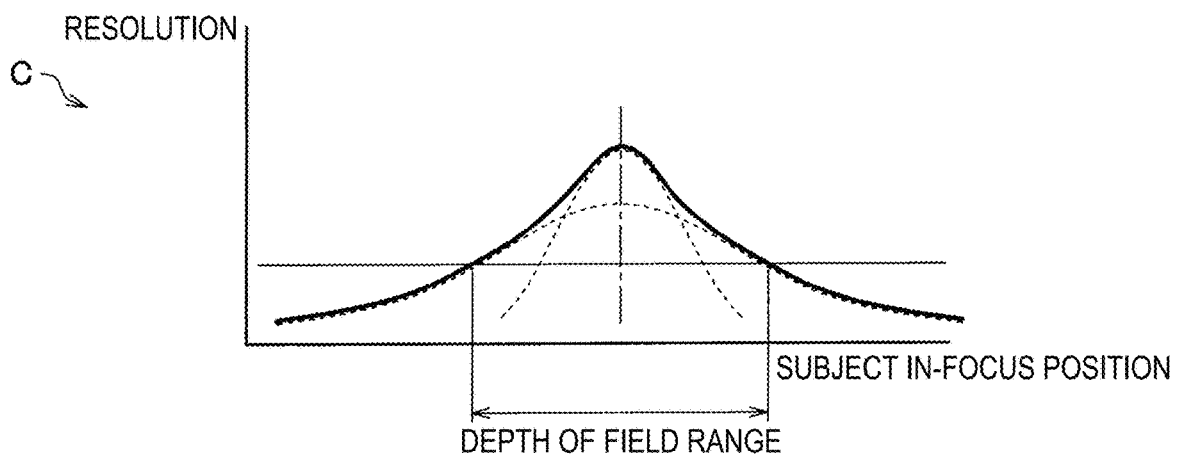

FIG. 10 is an explanatory diagram for explaining one example of the depth compositing process related to the image processing method according to the present embodiment. A of FIG. 10 illustrates one example of the relationship between depth of field and resolution in the medical captured image for the left eye captured by the imaging device with the left-eye optical system illustrated in A of FIG. 3. B of FIG. 10 illustrates one example of the relationship between depth of field and resolution in the medical captured image for the right eye captured by the imaging device with the right-eye optical system illustrated in A of FIG. 3. C in FIG. 10 illustrates one example of the result of executing the depth compositing process on the medical captured image for the left eye illustrated in A of FIG. 10 and the medical captured image for the right eye illustrated in B of FIG. 10.

As illustrated in A of FIG. 10, in the medical captured image for the left eye, the depth of field is narrow, but the resolving power is high. On the other hand, as illustrated in B of FIG. 10, in the medical captured image for the right eye, the depth of field is wide, but the resolving power is low.

For each portion where the medical captured image for the right eye and the medical captured image for the left eye correspond, the first depth compositing processing section 166 complements the medical captured image for the left eye with the higher-resolution medical captured image for the right eye. Therefore, the medical captured image for the left eye after the depth compositing process obtained as a result of the first depth compositing processing section 166 executing the depth compositing process becomes an image achieving both a deep subject depth and a high resolving power, as illustrated in C of FIG. 10.

The second depth compositing processing section 168 depth-composites the medical captured image for the right eye using the associated medical captured image for the left eye (one example of an other medical captured image). The depth compositing process in the second depth compositing processing section 168 is similar to the depth compositing process in the first depth compositing processing section 166 described with reference to FIG. 10. Therefore, the medical captured image for the right eye after the depth compositing process obtained as a result of the second depth compositing processing section 168 executing the depth compositing process becomes an image achieving both a deep subject depth and a high resolving power, as illustrated in C of FIG. 10.

The 3D compositing processing section 170 3D-composites the medical captured image for the right eye after the depth compositing process and the medical captured image for the left after the depth compositing process obtained by the depth compositing processes in each of the first depth compositing processing section 166 and the second depth compositing processing section 168. The 3D compositing process in the 3D compositing processing section 170 may be, for example, a process of processing the image signal to conform to any 3D representation method, such as "Line by Line" or "Side by Side".

By the functional configuration illustrated in FIG. 9, for example, the compositing processing section 164 is able to obtain a medical captured image for the right eye in which both a deeper depth of field and a higher resolution are potentially achieved as well as a medical captured image for the left eye in which both a deeper depth of field and a higher resolution are potentially achieved.

The image processing section 158 executes the association process and the compositing process related to the image processing method by including the functional configuration illustrated in FIG. 9, for example.

Note that the functional configuration of the image processing section 158 is not limited to the example illustrated in FIG. 9.

As described above, in the compositing processing section 164, the first depth compositing processing section 166 and the second depth compositing processing section 168 fulfill a role of executing the compositing process. Therefore, the compositing processing section 164 included in the image processing section 158 does not have to include the 3D compositing processing section 170.

Also, in the above, the processes related to the image processing method according to the present embodiment are expressed by the two processes of the association process and the compositing process, but the way in which the processes related to the image processing method according to the present embodiment are divided up is not limited to the example illustrated above. In other words, the image processing section 158 may also have a configuration depending on the way in which the processes related to the image processing method according to the present embodiment are divided up.

(2) Second Example of Processes Related to Image Processing Method

Next, as a second example of the processes related to the image processing method, an example of the processes related to the image processing method in the "case in which the multiple imaging devices are three or more imaging devices" will be described.

The three or more imaging devices refer to an "imaging device that captures the medical captured image for the right eye", an "imaging device that captures the medical captured image for the left eye", and "one or multiple imaging devices that capture a medical captured image to use in depth compositing". In the following, the "imaging device that captures the medical captured image for the right eye" will be designated the "first imaging device", while the "imaging device that captures the medical captured image for the left eye" will be designated the "second imaging device" in some cases. Also, in the following, each of the "one or multiple imaging devices that capture a medical captured image to use in depth compositing" will be designated the "third imaging device" in some cases.

Among the three or more imaging devices, the first imaging device and the second imaging device may be fixed, or may be set in any way by operations or the like by the user who uses the medical observation system 1000. Among the three or more imaging devices, an imaging device that corresponds to neither of the first imaging device and the second imaging device functions as the third imaging device.

The examples given below are examples of combinations of three or more imaging devices. Note that examples of combinations of three or more imaging devices obviously are not limited to the examples given below.

The in-focus position and the in-focus range of the first imaging device are the same as the in-focus position and the in-focus range of the second imaging device, and additionally, one or both of the in-focus position and the in-focus range of the third imaging device are different from the first imaging device and the second imaging device (for example, the combination illustrated in FIG. 5). In the case in which there are multiple third imaging devices, any or all of the multiple third imaging devices may have the same in-focus position and in-focus range.

In each of the first imaging device, the second imaging device, and the third imaging device, one or both of the in-focus position and the in-focus range are different (for example, the combination illustrated in FIG. 6). In the case in which there are multiple third imaging devices, any or all of the multiple third imaging devices may have the same in-focus position and in-focus range.

Even in the case in which the multiple imaging devices are three or more imaging devices, by a functional configuration similar to the functional configuration (including modifications) illustrated in FIG. 9, the image processing section 158 is able to obtain a medical captured image for the right eye in which both a deeper depth of field and a higher resolution are potentially achieved and a medical captured image for the left eye in which both a deeper depth of field and a higher resolution are potentially achieved".

Specifically, similarly to the association processing section 162 according to the first example, the association processing section 162 according to the second example associates each of the medical captured images for the right eye captured by the first imaging device, the medical captured image for the left eye captured by the second imaging device, and the medical captured image captured by the third imaging device.

Similarly to the first depth compositing processing section 166 according to the first example, the first depth compositing processing section 166 included in the compositing processing section 164 according to the second example depth-composites the medical captured image for the left eye using the associated other medical captured images (the medical captured image for the right eye captured by the first imaging device and the medical captured image captured by the third imaging device).

Similarly to the second depth compositing processing section 168 according to the first example, the second depth compositing processing section 168 included in the compositing processing section 164 according to the second example depth-composites the medical captured image for the right eye using the associated other medical captured images (the medical captured image for the left eye captured by the second imaging device and the medical captured image captured by the third imaging device).

Consequently, similarly to the compositing processing section 164 according to the first example, the compositing processing section 164 according to the second example is able to obtain a medical captured image for the right eye in which both a deeper depth of field and a higher resolution are potentially achieved as well as a medical captured image for the left eye in which both a deeper depth of field and a higher resolution are potentially achieved.

Also, the compositing processing section 164 executes the depth compositing process by additionally using the medical captured image captured by the third imaging device. Therefore, in the case of executing the processes related to the image processing method according to the second example, as the number of third imaging devices increases, it is possible to obtain higher-resolution medical captured images over the entire depth range from front to back.

[3] Example of Advantageous Effects Exhibited by Use of Image Processing Method According to Present Embodiment By using the image processing method according to the present embodiment, the advantageous effects illustrated below are exhibited, for example. Note that the advantageous effects exhibited by using the image processing method according to the present embodiment obviously are not limited to the examples illustrated below.

It is possible to treat both the medical captured image for the right eye and the medical captured image for the left eye as images achieving both a high resolving power and a deep depth of field. In other words, obtaining a medical captured image with an expanded depth while also maintaining a high resolving power is achievable with both the medical captured image for the right eye and the medical captured image for the left eye.

An observer who looks at a display screen displaying the medical captured image for the right eye and the medical captured image for the left eye after the depth compositing process is executed is able to see left and right images at the same resolution. Therefore, by using the image processing method according to the present embodiment, an advantageous effect of reducing eyestrain for the above observer is anticipated.

Since it is not necessary to configure the optical system of the imaging device to have separate optical paths, by adopting such a configuration, miniaturization of the imaging devices is achievable.

(Program According to Present Embodiment)

By having a program (for example, a program capable of executing the processes related to the image processing method according to the present embodiment) for causing a computer system to function as the medical observation apparatus according to the present embodiment (or the medical image processing apparatus according to the present embodiment) be executed by a processor or the like in the computer system, it is possible to potentially achieve both a deeper depth of field and a higher resolution in each of the medical observation system for the right eye and the medical observation system for the left eye. At this point, the computer system according to the present embodiment may be a single computer or multiple computers. A series of processes related to the image processing method according to the present embodiment is executed by the computer system according to the present embodiment.

Additionally, by having the program for causing a computer system to function as the medical observation apparatus according to the present embodiment (or the medical image processing apparatus according to the present embodiment) be executed by a processor or the like in the computer system, the advantageous effects exhibited by the display realized by the processes related to the image processing method according to the present embodiment described above can be exhibited.

It should be understood by those skilled in the art that various modifications, combinations, sub-combinations and alterations may occur depending on design requirements and other factors insofar as they are within the scope of the appended claims or the equivalents thereof.

For example, although the above illustrates the provision of a program (computer program) for causing a computer system to function as the medical observation apparatus according to the present embodiment (or the medical image processing apparatus according to the present embodiment), in the present embodiment, the above program may also be provided in conjunction with a recording medium on which the above program is stored.

The configuration described above illustrates one example of the present embodiment, and rightfully belongs to the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1) A medical image processing apparatus including:
an association processing section configured to associate multiple medical captured images in which an observation target is imaged by each of multiple imaging devices including imaging devices in which one or both of an in-focus position and an in-focus range are different; and a compositing processing section configured to depth-composite each of a medical captured image for a right eye and a medical captured image for a left eye among the multiple medical captured images by using an associated other medical captured image.

(2) The medical image processing apparatus according to (1), in which
the compositing processing section depth-composites by complementing each of the medical captured image for the right eye and the medical captured image for the left eye with the other medical captured image of a higher resolution.

(3) The medical image processing apparatus according to (1) or (2), in which
the association processing section associates the multiple medical captured images by extracting a characteristic portion from each of the multiple medical captured images and matching the extracted characteristic portions.

(4) The medical image processing apparatus according to (1) or (2), in which
the association processing section associates the multiple medical captured images by estimating a same subject included in each of the multiple medical captured images on the basis of settings information indicating settings of each of the multiple imaging devices.

(5) The medical image processing apparatus according to any one of (1) to (4), in which
the multiple imaging devices are two imaging devices, namely an imaging device that captures the medical captured image for the right eye and an imaging device that captures the medical captured image for the left eye,
the association processing section associates the medical captured image for the right eye and the medical captured image for the left eye, and
the compositing processing section depth-composites each of the medical captured image for the right eye and the medical captured image for the left eye by using the associated other medical captured image.

(6) The medical image processing apparatus according to any one of (1) to (4), in which
the multiple imaging devices are a first imaging device that captures the medical captured image for the right eye, a second imaging device that captures the medical captured image for the left eye, and one or multiple third imaging devices that capture a medical captured image to use in depth compositing.

(7) The medical image processing apparatus according to (6), in which
the first imaging device and the second imaging device have the same in-focus position and in-focus range, and
the other medical captured image used in depth compositing is a medical captured image captured by the one or multiple third imaging devices.

(8) The medical image processing apparatus according to (6), in which
in each of the first imaging device, the second imaging device, and the third imaging device, one or both of the in-focus position and the in-focus range are different.
(9) The medical image processing apparatus according to (1), further including:
a display control section configured to cause each of the depth-composited medical captured image for the right eye and the depth-composited medical captured image for the left eye to be displayed on a display screen.
(10) A medical observation apparatus including:
multiple imaging devices, each configured to image an observation target, including imaging devices in which one or both of an in-focus position and an in-focus range are different;
an association processing section configured to associate multiple medical captured images captured by each of the multiple imaging devices; and
a compositing processing section configured to depth-composite each of a medical captured image for a right eye and a medical captured image for a left eye among the multiple medical captured images by using an associated other medical captured image.
(11) The medical observation apparatus according to (10), further including:
an arm including multiple links joined to each other by one or multiple joint sections, in which
the multiple imaging devices are supported by the arm.
(12) The medical observation apparatus according to (10), in which
the multiple imaging devices are inserted into an inside of a body of a patient and images the inside of the body as the observation target.
(13) An image processing method, executed by a medical image processing apparatus, including:
associating multiple medical captured images in which an observation target is imaged by each of multiple imaging devices including imaging devices in which one or both of an in-focus position and an in-focus range are different; and
depth-compositing each of a medical captured image for a right eye and a medical captured image for a left eye among the multiple medical captured images by using an associated other medical captured image.

What is claimed is:

1. A medical image processing apparatus comprising:
circuitry configured to:
associate multiple medical images in which an observation target is imaged by each of multiple imaging devices including a first imaging device and a second imaging device located at a same position relative to the observation target; and
depth-composite each of a medical image for a right eye and a medical image for a left eye among the multiple medical images by using information obtained by a third imaging device, wherein one or both of an in-focus position and an in-focus range of the third imaging device is different from an in-focus position and an in-focus range of the at least one of the first imaging device and the second imaging device.

2. The medical image processing apparatus according to claim 1, wherein the first imaging device and the second imaging device have the same in-focus position and in-focus range.

3. The medical image processing apparatus according to claim 1, wherein one or both of an in-focus position and an in-focus range are different for the first imaging device and the second imaging device.

4. The medical image processing apparatus according to claim 1, wherein
the third imaging device is included in the multiple imaging devices, and
the information obtained by the third imaging device is an associated other medical image.

5. The medical image processing apparatus according to claim 4, wherein the in-focus range of the third imaging device is larger than the in-focus range of one of the first imaging device and the second imaging device.

6. The medical image processing apparatus according to claim 4, wherein the in-focus position is different for the first imaging device, the second imaging device and the third imaging device.

7. The medical image processing apparatus according to claim 1, wherein the circuitry is configured to depth-composite by complementing each of the medical images for the right eye and the medical image for the left eye with the other medical image of a higher resolution.

8. The medical image processing apparatus according to claim 1, wherein the circuitry is configured to associate the multiple medical images by extracting a characteristic portion from each of the multiple medical images and matching the extracted characteristic portions.

9. The medical image processing apparatus according to claim 1, wherein the circuitry is configured to associate the multiple medical images by estimating a same subject included in each of the multiple medical images on a basis of settings information indicating settings of each of the multiple imaging devices.

10. The medical image processing apparatus according to claim 1, wherein the multiple imaging devices are a first imaging device capturing the medical image for the right eye and a second imaging device capturing the medical image for the left eye, the circuitry is configured to: associate the medical image for the right eye and the medical image for the left eye, and
depth-composite each of the medical image for the right eye and the medical image for the left eye by using the associated other medical image.

11. The medical image processing apparatus according to claim 1, wherein the multiple imaging devices are the first imaging device capturing the medical image for the right eye, a second imaging device capturing the medical image for the left eye, and the one or multiple third imaging devices capturing a medical image to use in depth compositing.

12. The medical image processing apparatus according to claim 11, wherein
the first imaging device and the second imaging device have the same in-focus position and in-focus range, and
the other medical image used in depth compositing is a medical image captured by the one or multiple third imaging devices.

13. The medical image processing apparatus according to claim 11, wherein in each of the first imaging device, the second imaging device, and the third imaging device, one or both of the in-focus position and the in-focus range are different.

14. The medical image processing apparatus according to claim 1, wherein the circuitry is further configured to:
cause each of the depth-composited medical image for the right eye and the depth-composited medical image for the left eye to be displayed on a display screen.

15. The medical image processing apparatus according to claim 1, wherein a first medical image of the multiple medical images has a first resolution and a first field of view, a second medical image of the multiple medical images has a second resolution and a second field of view, the first resolution being greater than the second resolution and the second field of view being wider than the first field of view, and a depth-composite image of the first and second medical images has the first resolution and the second field of view.

16. The medical image processing apparatus according to claim 1, wherein each of the multiple imaging devices have an optical path through a common lens.

17. A medical observation apparatus comprising:
multiple imaging devices including a first imaging device and a second imaging device located at a same position relative to an observation target, each configured to image an observation target; and
circuitry configured to
associate multiple medical images captured by each of the first imaging device and the second imaging device; and
depth-composite each of a medical image for a right eye and a medical image for a left eye among the multiple medical images by using information obtained by a sensor, wherein one or both of an in-focus position and an in-focus range of the sensor is different from one or both of an in-focus position and an in-focus range of the at least one of the first imaging device and the second imaging device.

18. The medical observation apparatus according to claim 17, further comprising:
an arm including multiple links joined to each other by one or multiple joint sections, wherein the multiple imaging devices are supported by the arm.

19. The medical observation apparatus according to claim 17, wherein the multiple imaging devices are inserted into an inside of a body of a patient and images the inside of the body as the observation target.

20. An image processing method, executed by a medical image processing apparatus, comprising:
associating multiple medical images in which an observation target is imaged by each of multiple imaging devices including a first imaging device and a second imaging device located at a same position relative to the observation target; and
depth-compositing each of a medical image for a right eye and a medical image for a left eye among the multiple medical images by using information obtained by a sensor, wherein one or both of an in-focus position and an in-focus range of the sensor is different from one or both of an in-focus position and an in-focus range of the at least one of the first imaging device and the second imaging device.

21. The image processing method according to claim 20, wherein a first medical image of the multiple medical images has a first resolution and a first field of view, a second medical image of the multiple medical images has a second resolution and a second field of view, the first resolution being greater than the second resolution and the second field of view being wider than the first field of view, and a depth-composite image of the first and second medical images has the first resolution and the second field of view.

22. The image processing method according to claim 20, wherein each of the multiple imaging devices have an optical path through a common lens.

* * * * *